US007049133B2

(12) United States Patent
Kaempfer et al.

(10) Patent No.: US 7,049,133 B2
(45) Date of Patent: May 23, 2006

(54) REGULATION OF GENE EXPRESSION THROUGH MANIPULATION OF MRNA SPLICING AND ITS USES

(75) Inventors: Raymond Kaempfer, Jerusalem (IL); Farhat Osman, Sakhnin (IL); Nayef Jarrous, Shefaram (IL); Yitzhak Ben-Asouli, Kfar Hanagid (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 0 days.

(21) Appl. No.: 09/801,371

(22) Filed: Mar. 7, 2001

(65) Prior Publication Data

US 2002/0155569 A1    Oct. 24, 2002

Related U.S. Application Data

(63) Continuation of application No. PCT/IL99/00483, filed on Sep. 6, 1999.

(30) Foreign Application Priority Data

Sep. 7, 1998 (IL) ..................................... 126112
Oct. 26, 1998 (IL) ..................................... 126757

(51) Int. Cl.
C12N 15/00 (2006.01)
C12N 15/09 (2006.01)
C12N 15/63 (2006.01)
C12N 15/70 (2006.01)
C12N 15/74 (2006.01)

(52) U.S. Cl. ................... 435/320.1; 435/325; 435/455; 435/456; 435/69.1; 435/243; 435/358; 435/371; 435/372; 536/23.1; 536/23.4

(58) Field of Classification Search .................. 514/44; 435/320.1, 455, 325, 456, 69.1, 243, 358, 435/371, 372; 536/23.4, 23.1
See application file for complete search history.

(56) References Cited

U.S. PATENT DOCUMENTS 5,559,019 A    9/1996  Gui et al.
6,399,587 B1 *  6/2002  Mehtali et al. ............... 514/44

FOREIGN PATENT DOCUMENTS

EP    0309237    3/1989
WO    9421661    9/1994
WO    9727309    7/1997

OTHER PUBLICATIONS

Ngo et al., The Protein Folding Problem and Tertiary Structure Prediction, Birkhauser Boston, 1994, pp. 491-494.*
Chiu et al., Folding and Design, vol. 3, 1998, pp. 223-228.*
Alberts et al., Molecular Biology of the Cell, 3rd edition, Garland Publishing, New York, 1994, Figure 9-84.*
Adams et al., GenBank Accession No. T29839, US National Library of Medicine, Bethesda, MD, Sep. 6, 1995, accessed by PTO on Jul. 9, 2003.*
Osman F et al.; "A cis-acting element in the 3'-UTR of human TNF-alpha mRNA renders splicing dependent on activation of protein kinase PKR"; European Cytokine Network, (Sep. 1998), vol. 9, No. 3, p. 479.
N. Jarrous et al.; "2-Aminopurine selectively inhibits splicing of tumor necrosis factor alpha mRNA"; Mol. Cell. Biol.; vol. 16, No. 6, Jun. 1996, pp. 2814-2822.
S. Davis et al; "In vitro activation of the interferon-induced, double-stranded RNA-dependent protein kinase PKR by RNA from the 3' untranslated regions of human alpha-tropomyosin", Proc. Natl. Acad. Sci, vol. 93, Jan. 1996, pp. 508-513.
J. Wang et al.; "Regulation of pre-mRNA splicing in metazoa"; Current Opinion in Genetics & Development, vol. 7, No. 2, Apr. 1997, pp. 205-211.
Groskreutz et al.; "Transient Expression: Increased Gene Expression in Mammalian Cell Lines Using Padvantage (TM) DNA As Co-Transfectant"; Promega Notes, vol. 48, pp. 8-12.
F. Osman et al.; "A cis-acting element in the 3'-untranslated region of human TNF-alpha mRNA renders splicing dependent on the activating of protein kinase PKR"; Genes & Development, vol. 13, No. 24, Dec. 1999, pp. 3280-3293.
Osman F et al., (1999) "A cis-acting elements in the 3'-untranslated region of human TNF-alpha mRNA renders splicing dependent on the activation of protein kinase PKR" Genes Development, 13(24):3280-3293.
Autieri MV et al., (1998) "IRT-1, a novel interferon-gamma-responsive transcript encoding a growth-suppressing basic leucine zipper protein" J Biol Chem. 273(24):14731-14737.
Besse S et al., (1998) "Ultrastructural localization of interferon-inducible double-stranded RNA-activated enzymes in human cells" Exp Cell Res 239(2):379-392.

(Continued)

Primary Examiner—Joseph Woitach
Assistant Examiner—Brian Whiteman
(74) Attorney, Agent, or Firm—Baker Botts LLP

(57) ABSTRACT

A cis-acting nucleotide sequence which is capable of rendering the removal of introns from a precursor transcript encoded by a gene, which gene harbors at least one such cis-acting nucleotide sequence, occurring during the production of mRNA of a gene, dependent upon activation of a trans-acting factor. The trans-acting factor is an RNA-activated protein kinase which is capable of phosphorylating the α-subunit of eukaryotic initiation factor 2. The trans-acting factor is preferably, the RNA-activated protein kinase (PKR). The cis-acting nucleotide sequence can be derived from the 3' untranslated region of the human tumor necrosis factor α gene (TNF-α3'-UTR) and may comprise the nucleotide sequence as denoted by SEQ ID NO:1 or biologically functional fragments, derivatives, mutants and homologues thereof.

37 Claims, 14 Drawing Sheets

OTHER PUBLICATIONS

Bevilacqua PC et al., (1998) "Binding of the protein kinase PKR to RNAs with secondary structure defects: role of the tandem A-G mismatch and noncontiguous helixes" *Biochemistry* 37(18):6303-6316.

Chu WM et al., (1998) "Potential Alu function: regulation of the activity of double-stranded RNA-activated kinase PKR" *Mol Cell Biol* 18(1):58-68.

Chung KC et al., (1998) "Raf and fibroblast growth factor phosphorylate Elk1 and activate the serum response element of the immediate early gene pip92 by mitogen-activated protein kinase-independent as well as -dependent signaling pathways" *Mol Cell Biol.* 18(4):2272-2281.

Lewis T et al., (1998) "Mapping of a minimal AU-rich sequence required for lipopolysaccharide-induced binding of a 55-kDa protein on Tumor necrosis factor-alpha mRNA" *J Biol Chem* 273(22):13781-13786.

Osman et al. (1998) "A Cis-acting Element in the 3' UTR of human TNF-α mRNA renders splicing dependant on Activatino of Protein Kinase PKR" *European Cytokine Network* vol. 9, Supp. No. 3, Abstract No. 479.

Circle DA et al., (1997) "Surprising specificity of PKR binding to delta agent genomic RNA" *RNA* 3(4):438-448.

Kerkhoff E et al., (1997) "Induction of cell proliferation in quiescent NIH 3T3 cells by oncogenic c-Raf-1" *Mol Cell Biol* 17(5):2576-2586.

Mijatovic T et al., (1997) "Interleukin-4 and -13 inhibit tumor necrosis factor-alpha mRNA translational activation in lipopolysacharide-induced mouse macrophages" *J Biol Chem* 272(22):14394-14398.

Misteli T et al., (1997) "The dynamics of a pre-mRNA splicing factor in living cells" *Nature* 387(6632):523-527.

Wang, J et al., (1997) "Regulation of pre-mRNA splicing in metazoa" *Curt Opin Genet Dev* 7(2):205-211.

Webster J et al., (1997) "Intronic sequences modulate the sensitivity of beta-lactoglobulin transgenes to position effects" *Gene* 193(2):239-243.

Wu S et al., (1997) "A model for the double-stranded RNA (dsRNA)-dependent dimerization and activation of the dsRNA-activated protein kinase PKR" *J Biol Chem* 272(2):1291-1296.

Bevilacqua PC et al., (1996) "Minor-groove recognition of double-stranded RNA by the double-stranded RNA-binding domain from the RNA-activated protein kinase PKR" *Biochemistry* 35(31):9983-9994.

Colwill K et al., (1996) "The Clk/Sty protein kinase phosphorylates SR splicing factors and regulates their intranuclear distribution" *EMBO J* 15(2):265-275.

Davis S et al., (1996) "In vitro activation of the interferon-induced, double-stranded RNA-dependent protein kinase PKR by RNA from the 3' untranslated regions of human alpha-tropomyosin" *Proc Natl Acad Sci USA* 93(1):508-513.

Elia A et al., (1996) "Regulation of the double-stranded RNA-dependent protein kinase PKR by RNAs encoded by a repeated sequence in the Epstein-Barr virus genome" *Nucleic Acids Res.* 24(22):4471-4478.

Jarrous N et al., (1996) "2-Aminopurine selectively inhibits splicing of tumor necrosis factor alpha mRNA" *Mol Cell Biol* 16(6):2814-2822.

Robertson HD et al., (1996) "The regulation of the protein kinase PKR by RNA" *Biochimie* 78(11-12):909-914.

Robertson HD et al., (1996) "Paradoxical interactions between human delta hepatitis agent RNA and the cellular protein kinase PKR" *J Virol* 70(8):5611-5617.

Yin DX et al., (1996) "Tetracycline-controlled gene expression system achieves high-level and quantitative control of gene expression" *Anal Biochem* 235(2):195-201.

Biragyn A et al., (1995) "Lipopolysaccharide-induced expression of TNF-alpha gene in the macrophage cell line ANA-1 is regulated at the level of transcription processivity" *J Immunol* 155(2):674-683.

Clarke PA et al., (1995) "Interactions between the double-stranded RNA binding motif and RNA: definition of the binding site for the interferon-induced protein kinase DAI (PKR) on adenovirus VA RNA" *RNA* 1(1):7-20.

Der SD et al., (1995) "Involvement of the double-stranded-RNA-dependent kinase PKR in interferon expression and interferon-mediated antiviral activity" *Proc Natl Acad Sci USA* 92(19):8841-8845.

Donze O et al., (1995) "Abrogation of translation initiation factor eIF-2 phosphorylation causes malignant transformation of NIH 3T3 cells" *EMBO J* 14(15):3828-3834.

Gerez L et al., (1995) "Post-transcriptional regulation of human interleukin-2 gene expression at processing of precursor transcripts " *J Biol Chem* 270(33):19569-19575.

Jeffrey IW et al., (1995) "Nuclear localization of the interferon-inducible protein kinase PKR in human cells and trasfected mouse cells" *Exp Cell Res* 218(1):17-27.

Neel H et al., (1995) "Regulation of pre-mRNA processing by src" *Curr Biol* 5(4):413-422.

Petitclerc D et al., (1995) "The effect of various introns and transcription terminators on the efficiency of expression vectors in various cultured cell lines and in the mammary gland of transgenic mice" *J Biotech* 40(3):169-178.

Schmedt C et al., (1995) Functional characterization of the RNA-binding domain and motif of the double-stranded RNA-dependent protein kinase DAI (PKR)" *J Mol Biol* 249(1):29-44.

Srivastava SP et al., (1995) "Calcium depletion from the endoplasmic reticulum activates the double-stranded RNA-dependent protein kinase (PKR) to inhibit protein synthesis" *J Biol Chem* 270(28):16619-16624.

Umlauf SW et al., (1995) "Regulation of interleukin 2 gene expression by CD28 costimulation in mouse T-cell clone both nuclear and cytoplasmic RNAs are regulated with complex kinetics" *Mol Cell Biol* 15(6):3197-3205.

Chalfie M et al., (1994) "Green fluorescent protein as a marker for gene expression" *Science* 263(5148):802-805.

Gui JF et al., (1994) "A serine kinase regulates intracellular localization of splicing factors in the cell cycle" *Nature* 369(6482):678-682.

Groskreutz et al. (1994) "Incresed Gene Expression in Mammalian Cell Lines Using pAdVantage™ DNA as a Co-Transfectant" Promega Notes Magazine 48:8-12.

Henry GL et al., (1994) "Mechanism of interferon action. Translational control and the RNA-dependent protein kinase (PKR): antagonists of PKR enhance the translational activity of mRNAs that include a 161 nucleotide region from reovirus S1 mRNA" *J Biol Regul Homeost Agents* 8(1):15-24.

Jarrous N et al., (1994) "Induction of human interleukin-1 gene expression by retinoic acid and its regulation at processing of precursor transcripts" *J Biol Chem* 269(37):23141-23149.

Maitra RK et al., (1994) "HIV-1 TAR RNA has an intrinsic ability to activate interferon-inducible enzymes" *Virology* 204(2):823-827.

Simonsen CC et al., (1994) "The molecular biology of production cell lines" *Biologicals* 22(2):85-94.

Tanaka H et al., (1994) "Mechanism of interferon action: structure of the mouse PKR gene encoding the interferon-inducible RNA-dependent protein kinase" *Proc Natl Acad Sci USA* 91(17):7995-7999.

Wilmut I et al., (1994) "Strategies for production of pharmaceutical proteins in milk" *Reprod Fertil Dev* 6(5):625-630.

Davies et al., (1993) "The E3L and K3L vaccinia virus gene products stimulate translation through inhibition of the double-stranded RNA-dependent protein kinase by different mechanisms" *J Virol* 67(3):1688-1692.

Hu Y et al., (1993) "2-Aminopurine inhibits the double-stranded RNA-dependent protein kinase both in vitro and in vivo" *J Interferon Res* 13(5):323-328.

Meurs EF et al., (1993) "Tumor suppressor function of the interferon-induced double-stranded RNA-activated protein kinase" *Proc Natl Acad Sci USA* 90(1):232-236.

Samuel CE (1993) "*The eIF-2 alpha protein kinases, regulators of translation in eukaryotes from yeasts to humans*" *Biol Chem* 268(11):7603-7606.

Thomis DC et al., (1993) "Mechanism of interferon action: evidence for intermolecular autophosphorylation and autoactivation of the interferon-induced, RNA-dependent protein kinase PKR" *J Virol* 67(12):7695-7700.

Banner CD et al. (1992) "A method for characterization of endogenous ligands to orphan receptors belonging to the steroid hormone receptor superfamily—isolation of progesterone from pregnancy plasma using progesterone receptor ligand-binding domain" *Anal Biochem* 200(1):163-170.

Clark AJ et al., (1992) "Rescuing transgene expression by co-integration" *Biotechnology* 10(11):1450-1454.

Davies MV et al., (1992) "The vaccinia virus K3L gene product potentiates translation by inhibiting double-stranded-RNA-activated protein kinase and phosphorylation of the alpha subunit of eukaryotic initiation factor 2" *J Virol* 66(4):1943-1950.

Gossen M et al., (1992) "Tight control of gene expression in mammalian cells by tetracycline-responsive promoters" *Proc Natl Acad Sci USA* 89(12):5547-5551.

Koromilas A. et al., (1992) "Malignant transformation by a mutant of the IFN-inducible dsRNA-dependent protein kinase" *Science* 257(5077):1685-1689.

Kruys V et al., (1992) "Constitutive activity of the tumor necrosis factor promoter is canceled by the 3' untranslated region in nonmacrophage cell lines; a trans-dominant factor overcomes this suppressive effect" *Proc Natl Acad Sci USA* 89(2):673-677.

St. Johnston D et al., (1992) "A conserved double-stranded RNA-binding domain" *Proc Natl Acad Sci USA* 89(22):10979-10983.

Hershey JW, (1991) "Translational control in mammalian cells" *Annu Rev Biochem* 60:717-755.

Whitelaw CB et al., (1991) "Targeting expression to the mammary gland: intronic sequences can enhance the efficiency of gene expression in transgenic mice" *Transgenic Res* 1(1):3-13.

Goldfeld A. et al., (1990) "Human tumor necrosis factor alpha gene regulation by virus and lipopolysaccharide" *Proc Natl Acad Sci USA* 87(24):9769-9773.

Kaufmann RJ, (1990) "Vectors used for expression in mammalian cells" *Methods Enzymol* 185: 487-511.

Ko MS et al., (1989) "An auto-inducible vector conferring high glucocorticoid inducibility upon stable transformant cells" *Gene* 84(2):383-389.

Zuker M, (1989) "On finding all suboptimal foldings of an RNA molecule" *Science* 244(4900):48-52.

Buchman AR et al., (1988) "Comparison of intron-dependent and intron-independent gene expression" *Mol Cell Biol* 8(10):4395-4405.

Figge J et al., (1988) "Stringent regulation of stably integrated chloramphenicol acetyl transferase genes by *E. coli* lac repressor in monkey cells" Cell 52(5):713-722.

Zinn K et al., (1988) "2-Aminopurine selectively inhibits the induction of beta-interferon, c-fos, and c-myc gene expression" *Science* 240(4849):210-213.

Caput D et al., (1986) "Identification of a common nucleotide sequence in the 3'-untranslated region of mRNA molecules specifying inflammatory mediators" *Proc Natl Acad Sci USA* 83(6):1670-1674.

Wurm FM et al., (1986) "Inducible overproduction of the mouse c-myc protein in mammalian cells" *Proc Natl Acad Sci USA* 83(15):5414-5418.

Karin M et al., (1984) "Activation of a heterologous promoter in response to dexamethasone and cadmium by metallothionein gene 5'-flanking DNA" *Cell* 36(2):371-379.

Pennica D et al., (1984) "Human tumour necrosis factor: precursor structure, expression and homology to lymphotoxin" *Nature* 312(5996):724-729.

Gorman CM et al., (1982) "Recombinant genomes which express chloramphenicol acetyltransferase in mammalian cells" *Mol Cell Biol* 2(9):1044-1051.

Rosen H et al., (1981) "Messenger ribonucleic acid sepcificity in the inhibition of eukaryotic translation by double-stranded ribonucleic acid" *Biochemistry* 20(11):3011-3020.

Farrell PJ et al., (1977) "Phosphorylation of initiation factor eIF-2 and the control of reticulocyte protein synthesis" *Cell* 11(1):187-200.

Legon S et al., (1974) "The effect of cyclic AMP and related compounds on the control of protein synthesis in reticulocyte lysates" *Biochemical and Biophysical Research Communication* 56(3):745-752.

Yitzhak et al. (2002) "Human Interferon-γ mRNA Autoregulates Its Translation Through a Pseudoknot tha Activates the Interferon-Inducible Protein Kinase PKR" *Cell*, 108:221-232.

Bakheet et al. (2001) "ARED: Human AU-rich element-containing mRNA Database Reveals an Unexpectedly Diverse Functional Repertoire of Encoded Proteins" *Nucleic Acids Res.*. 29(1):246-254.

Ron & Harding (2000) "PERK and Translational Control by Stress in the Endoplasmic Reticulum" *Translational Control of Gene Expression* 547-560.

Farrell et al. (1977) "Phosphorylation of Initiation Factor eIF-2 and the Control of Reticulocyte Protein Synthesis" *Cell* 11:187-200.

Osman F et al., (1999) "A cis-acting elements in the 3'-untranslated region of human TNF-alpha mRNA renders splicing dependent on the activation of protein kinase PKR" *Genes Development*, 13(24):3280-3293.

Autieri MV et al., (1998) "IRT-1, a novel interferon-gamma-responsive transcript encoding a growth-suppressing basic leucine zipper protein" *J Biol Chem.* 273(24):14731-14737.

Besse S et al., (1998) "Ultrastructural localization of interferon-inducible double-stranded RNA-activated enzymes in human cells" *Exp Cell Res* 239(2):379-392.

Bevilacqua PC et al., (1998) "Binding of the protein kinase PKR to RNAs with secondary structure defects: role of the tandem A-G mismatch and noncontiguous helixes" *Biochemistry* 37(18):6303-6316.

Chu WM et al., (1998) "Potential Alu function: regulation of the activity of double-stranded RNA-activated kinase PKR" *Mol Cell Biol* 18(1):58-68.

Chung KC et al., (1998) "Raf and fibroblast growth factor phosphorylate Elk 1 and activate the serum response element of the immediate early gene pip92 by mitogen-activated protein kinase-independent as well as -dependent signaling pathways" *Mol Cell Biol.* 18(4):2272-2281.

* cited by examiner

|  |  |  | Splicing Inhibition by 2-AP | PKRΔ6 |
|---|---|---|---|---|
| FIG. 1A | 5'α CAT / AnSV40 | p5'CAT | − | nd |
| FIG. 1B | 5'α CAT 3'α / An(α) | p5'CAT(3'UTR-α) | − | nd |
| FIG. 1C | 5'α ex1 ex2 ex3 ex4 3'UTRα / E P An(α) | pTNF-α | + | nd |
| FIG. 1D | 5'α ex1 ex2 ex3 ex4 / An(β) | pTNF-α(Δ3'UTR) | − | − |
| FIG. 1E | 5'β ex1 ex2 ex3 ex4 3'β / An(β) | pTNF-β | − | − |
| FIG. 1F | 5'β ex1 ex2 ex3 ex4 3'α / An(α) | pTNF-β(3'UTR-α) | + | nd |
| FIG. 1G | 5'β ex1 ex2 ex3 ex4 | pTNF-β(Δ3'UTR) | − | nd |
| FIG. 1H | 5'α ex1 ex2 ex3 ex4 3'β / An(β) | pTNF-α(3'UTR-β) | − | nd |
| FIG. 1I | 5'α ex1 ex2 ex3 ex4 / An(β) | pTNF-α(3'UTR-αEP) | + | + |
| FIG. 1J | 5'β ex1 ex2 ex3 ex4 / An(β) | pTNF-β(3'UTR-αEP) | + | + |
| FIG. 1K | 5'α ex1 ex2 ex3 ex4 / An(β) | pTNF-α(Δ3'UTR)i3EP | + | + |

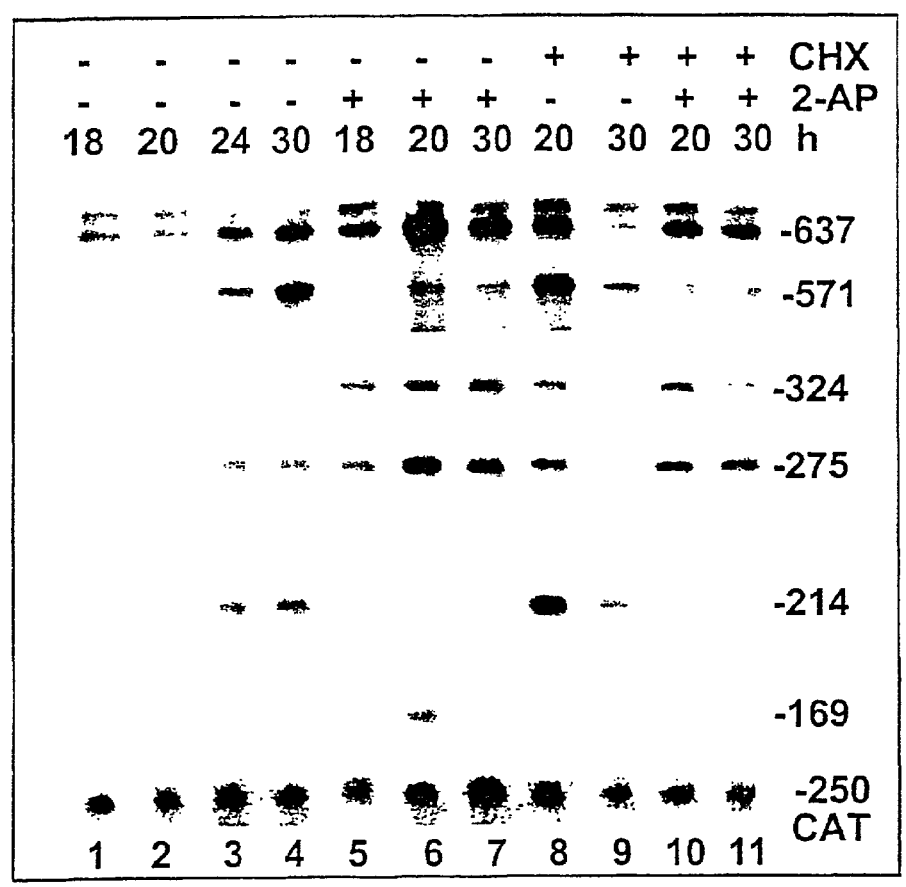

FIG. 4A
TNF-α 3'UTR
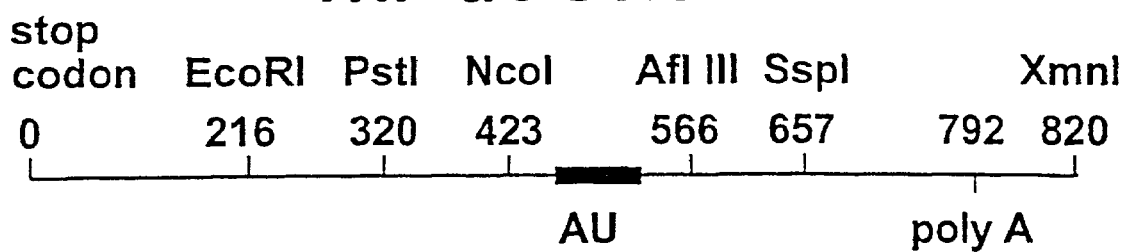
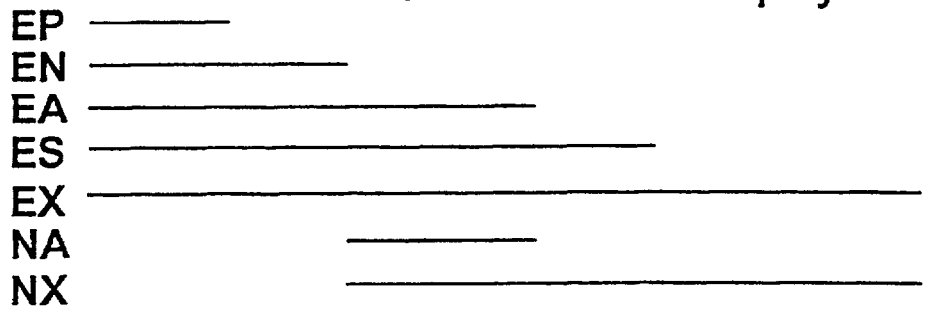

FIG. 5A
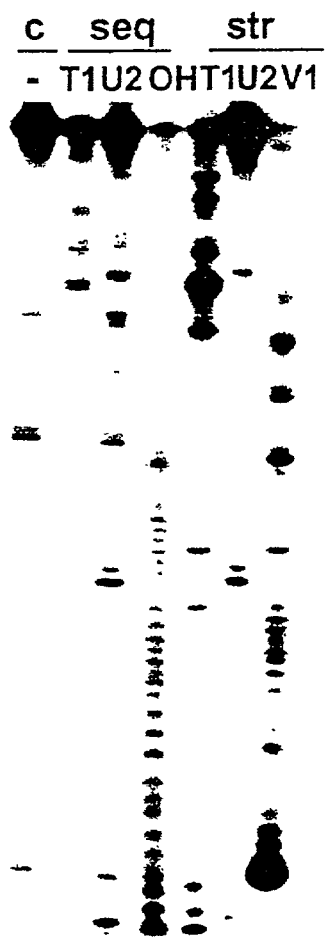
FIG. 5B
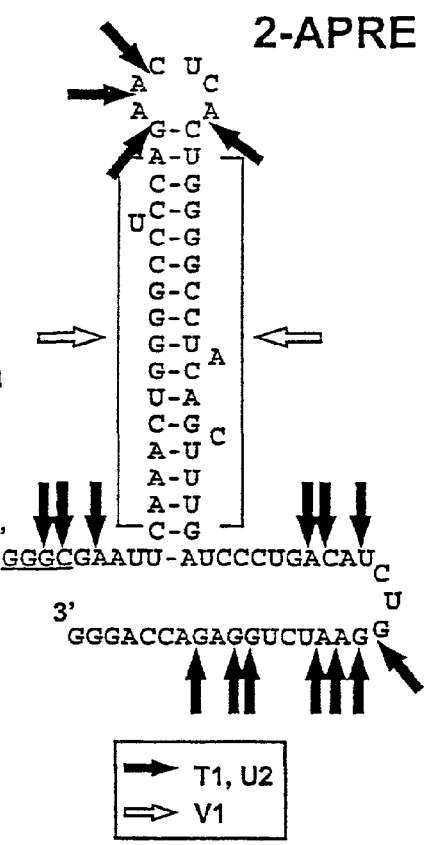
FIG. 5C
```
H.sapiens     GAAUUCAAACUGGGGCCUCCAGAACUCACUGGGGCCUACAGCUUU-GAUCC
S.scrofa      GAAUUGGAACUGGGGCUUCCAGA-CUCGCUGGGGUCCUUGGGUUUGGAUUC
O.cuniculus   GCAUUCAAACUGAGGCUUCCAGGACUCACUGGGGCCUUCAGAACUCCAUUC
B.taurus      ------------------UCCAGAACUCCCUGGGGUCCACAGCUU-------
C.hircus      -------------GGGCUCCAGAAGUUGCUGGUGCCU---------------
```

SEQUENCE LISTING

<160> NUMBER OF SEQ ID NOS: 12

<210> SEQ ID NO 1
<211> LENGTH: 104
<212> TYPE: DNA
<213> ORGANISM: Homo sapiens

<400> SEQUENCE: 1
gaattcaaac tggggcctcc agaactcact ggggcctaca gctttgatcc ctgacatctg    60
gaatctggag accagggagc ctttggttct ggccagaatg ctgc                    104

<210> SEQ ID NO 2
<211> LENGTH: 43
<212> TYPE: DNA
<213> ORGANISM: Homo sapiens

<400> SEQUENCE: 2
tcaaactggg gcctccagaa ctcactgggg cctacagctt tga                     43

<210> SEQ ID NO 3
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 3
ccgctcgaga attcaaactg ggcctcc                                       28

<210> SEQ ID NO 4
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 4
ccgctcgagt gcagcattct ggccagaacc                                    30

<210> SEQ ID NO 5
<211> LENGTH: 104
<212> TYPE: DNA
<213> ORGANISM: Homo sapien

<400> SEQUENCE: 5
gcagcattct ggccagaacc aaaggctccc tggtctccag attccagatg tcagggatca    60
aagctgtagg ccccagtgag ttctggaggc cccagtttga attc                    104

<210> SEQ ID NO 6
<211> LENGTH: 43
<212> TYPE: DNA
<213> ORGANISM: Homo sapien

<400> SEQUENCE: 6
tcaaagctgt aggccccagt gagttctgga ggccccagtt tga                     43

<210> SEQ ID NO 7
<211> LENGTH: 81
<212> TYPE: RNA
<213> ORGANISM: Homo sapien

<400> SEQUENCE: 7
gggcgaauuc aaacuggggc cuccagaacu cacuggggcc uacagcuuug aucccugaca    60

-continued

```
ucuggaaucu ggagaccagg g                                                    81

<210> SEQ ID NO 8
<211> LENGTH: 50
<212> TYPE: RNA
<213> ORGANISM: Homo sapien

<400> SEQUENCE: 8 gaaucaaac uggggccucc agaacucacu ggggccuaca gcuugaucc                        50

<210> SEQ ID NO 9
<211> LENGTH: 50
<212> TYPE: RNA
<213> ORGANISM: Sus scrofa

<400> SEQUENCE: 9
gaauuggaac uggggcuucc agacucgcug ggguccuugg guuuggauuc                      50

<210> SEQ ID NO 10
<211> LENGTH: 51
<212> TYPE: RNA
<213> ORGANISM: Oryctolagus cuniculus

<400> SEQUENCE: 10
gcauucaaac ugaggcuucc aggacucacu ggggccuuca gaacuccauu c                    51

<210> SEQ ID NO 11
<211> LENGTH: 27
<212> TYPE: RNA
<213> ORGANISM: Bos taurus

<400> SEQUENCE: 11
uccagaacuc ccugggguccc acagcuu                                             27

<210> SEQ ID NO 12
<211> LENGTH: 24
<212> TYPE: RNA
<213> ORGANISM: Capra hircus

<400> SEQUENCE: 12
gggcuccaga aguugcuggu gccu                                                 24
```

US 7,049,133 B2

REGULATION OF GENE EXPRESSION THROUGH MANIPULATION OF MRNA SPLICING AND ITS USES

This application is a continuation of copending International application PCT/IL99/00483 filed Sep. 6, 1999, which is incorporated by reference herein, claiming priority from Israeli application Nos. 126112 filed Sep. 7, 1998, and 126757 filed Oct. 26,1998. The International application was published in English on March 16, 2000, by the International Bureau.

FIELD OF THE INVENTION

The invention relates to cis-acting genetic elements that render the removal of introns from precursor transcripts encoded by a gene of interest, and thereby the production of mRNA of such gene, which harbors one or more of said elements, dependent upon the activation of a trans-acting factor, the trans-acting factor being an RNA-activated protein kinase capable of phosphorylated the α-subunit of eukaryotic translation initiation factor 2. The invention further relates to vectors for implementing regulation of gene expression at the level of mRNA splicing by means of said elements, for therapeutical as well as biotechnological purposes.

BACKGROUND OF THE INVENTION

Throughout this application various publications are referenced by Arab numerals within square parentheses. Full citations for these references may be found at the end of the specification immediately preceding the claims. The disclosures of these publications in their entireties are hereby incorporated into this application in order to more fully describe the state of the art as known to those skilled therein as of the date of the invention described and claimed herein.

When producing recombinant proteins in eukaryotic cells for biopharmaceutical and biotechnological purposes, the level of expression is a central parameter which controls the economy of the project. When the desired protein is present in the culture medium or cellular extract at low concentrations, its recovery will entail more extensive protein purification and lower final yield. However, high constitutive expression can in some instances lead to counterselection of the expressing cells during their proliferation phase, obstructing expression of a pharmaceutically or technologically relevant secreted protein to high levels in cell culture. Hence, there is a critical need for efficient and regulated expression vectors.

Improving the design of the expression vectors is also critical for gene therapy as illustrated by the often suboptimal levels of expression which have been observed in clinical trials. In this context, transgenic animals provide an appropriate model for testing gene therapy constructs, where an ability to regulate expression is of paramount importance.

In the long term, transgenic animals or plants will provide an alternative to large scale cell culture for the production of massive amounts of proteins or other gene products such as RNA and this production will require careful regulation of expression of the gene encoding a desired product. With the development of gene transfer techniques that allow the generation of transgenic animals or plants came the possibility of producing transgenic livestock functioning as animal bioreactors as an alternative strategy to cell culture systems for protein production [1]. For instance, protein secretion in the milk of large mammals could provide a cost-effective route for the production of large amounts of valuable proteins. As yet this technology is still in development and needs optimization, and there is a general requirement for methods to improve productivity.

Regulated expression could be achieved by several routes. Efforts to improve the design of expression vectors for biotechnological purposes have focused on transcriptional control [1–4] in an attempt to achieve both high levels of transcription and externally regulatable transcription, and to some extent by control of translation. Large-scale cell culture production of biopharmaceutical generally is accomplished by use of constitutive high-level expression vectors [5, 6]. For expression of heterologous proteins that are toxic, or impose a negative effect on cell growth, a regulated expression system is highly desirable [5, 6]. This will allow for propagation of the production cells to high density before turning on expression of the desired protein. This was done previously by use of vectors with inducible transcription [7–11]. In most of these systems, however, the range over which expression can be controlled remains limited, thus inviting improvement.

This invention deals with another major level of control of gene expression which has received little attention up to now: mRNA splicing, which is the processing of precursor transcripts into mature mRNA containing only exon sequences, by excision of introns at the RNA level in the cell nucleus. The mRNA splicing step is a good candidate for control since evidence exists that this mechanism functions in vivo [12, 13]. There are several examples of genes requiring a splicing event for mRNA production [24] and an intron generally is included in pharmaceutically employed expression vectors [5, 6]. For complementary DNA (cDNA) expression, the contribution of the intron to final product formation seems to be cDNA-specific but the mechanism of intron action remains largely unknown [25]. To date, little effort has been directed at regulation expression of genes for biotechnological use or gene therapy at the mRNA splicing step. Regulation of mRNA splicing would be useful for regulating expression of genes that have been transferred, be it into cell lines, the germline or somatic tissues.

Expression of several cytokine genes is highly regulated at splicing of precursor transcripts [12, 13, 27–29]. Thus, shortly after the onset of induction of human interleukin-2 (IL-2) and interleukin-1β (IL-1β) genes, the flow of nuclear precursor transcripts into mature mRNA becomes blocked despite the fact that transcription, once activated by an inducer, continues unabated for an extensive period. Expression of IL-2 and IL-1β mRNA is superinduced by two orders of magnitude in the presence of translation inhibitors, without a significant increase in primary transcription or mRNA stability. Instead, splicing of precursor transcripts is greatly facilitated [13, 27].

Expression of the human tumor necrosis factor-α (TNF-α) gene is also regulated at splicing [13]. 2-Aminopurine (2-AP) blocks expression of TNF-α mRNA in primary human lymphoid cells. An adenine isomer, 2-AP inhibits specific kinases that phosphorylate the α-subunit of eukaryotic translation initiation factor 2 (eIF2α) [17], including the RNA-activated protein kinase, PKR [30]. 2-AP does not inhibit human TNF-α gene expression at transcription, nor does it affect mRNA stability. Instead, splicing of short-lived TNF-α precursor transcripts into mRNA is blocked when 2-AP is present during induction, causing pre-mRNA to accumulate at the expense of mRNA; stability of TNF-α precursor transcripts is unaffected [13]. 2-AP blocks splicing of TNF-α precursor transcripts at multiple splice junctions. Neither the human IL-1β nor TNF-β gene shows such regulation. A 2-AP-sensitive component, expressed in functional form before induction, regulates splicing of TNF-α mRNA [13].

PKR, an RNA-activated Ser/Thr protein kinase, is a major negative regulator of translation [14, 15]. PKR is expressed constitutively in most cells but is induced by viruses, double-stranded RNA (dsRNA) and interferons [16]. Activation of PKR requires its trans-autophosphorylation which is facilitated by RNA, especially by dsRNA [15]. PKR phosphorylates eIF2α, blocking GDP/GTP exchange [17] and preventing the recycling of eIF2 between rounds of initiation of translation [18]. Thus, activation of PKR triggers an inhibition of protein synthesis. Dominant-negative mutants of PKR have been described that inhibit trans-autophosphorylation of the wild type enzyme, obligatory for its activation [19–21].

Activation of PKR requires its dimerization on RNA [22, 23] and thereby depends critically on its binding to RNA [23]. PKR contains two tandem double-stranded RNA binding motifs found in diverse proteins such as *Drosophila* staufen, ribosomal protein S5 and *E. coli* RNase III [26]. Perfectly matched dsRNA having the A conformation as well as certain other RNAs, including hepatitis delta agent RNA [31], reovirus S1 3'-UTR [32] and human α-tropomyosin 3'-UTR [33] activate PKR in vitro while adenovirus VA RNA [34] and Alu RNA bind to PKR and thereby inhibit its activation [35]. Both the activation of PKR and its inhibition require highly ordered RNA structures, rather than a specific sequence. Certain highly structured RNAs can be activators or inhibitors of PKR even when they contain imperfectly matched base-paired domains, such as human delta hepatitis agent RNA [26] or VA RNA [34]. The RNA-binding domain in PKR [36] requires 11–13 bp of dsRNA for binding [22, 37, 38] and can tolerate non-Watson-Crick structures [39]. Moreover, noncontiguous short helices of RNA can cooperate in binding of PKR and thereby, in its activation [39].

PKR was detected in cell nucleoplasm in an underphosphorylated state [40]. Upon induction by interferon, aggregates of PKR are colocalized with interchromatin granule clusters [41] known to contain significant amounts of spliceosomal components and to be involved in spliceosome assembly, sorting and recycling [42]. Modified splicing factors are recruited from these clusters into perichromatin fibrils where gene transcription occurs, facilitating cotransciptional RNA processing [42]. However, no functional connection between PKR and splicing was reported prior to this invention.

The TNF-α3'-untranslated region (3'-UTR) has multiple roles in regulating expression of TNF-α mRNA. It downregulates the murine TNF-α promoter at transcription [43] and harbors an AU-rich determinant of mRNA instability [44]. This AU-rich motif mediates translational inhibition by IL4 and IL-13 [45] and activation of translation by lipopolysaccharide [14] which induces formation of protein complexes that bind specifically to the nonanucleotide UUAUUUAUU [46]. However, no functional role for the TNF-α3'-UTR, or for a 3'-UTR as such, in the regulation of mRNA splicing was reported prior to this invention.

This invention describes the introduction of a novel cis-acting element, preferably within an expression construct, into a gene of interest, in order to render splicing of mRNA expressed by this gene dependent on the activation of an RNA-activated eIF2α kinase, thereby imparting on the expression of this gene a regulation at the mRNA splicing step by the novel cis-acting sequence element, through manipulation of the expression vector on one hand and application of methods known in the art to modulate the expression and/or activity of the RNA-activated eIF2α kinase in the recipient cells or organism on the other hand. Thus, the invention provides a novel solution to attain a regulated system for production of proteins of interest and to optimize expression and yield of such protein.

SUMMARY OF THE INVENTION

The present invention relates to cis-acting nucleic acid sequences which render the removal of intron/s from a precursor transcript encoded by a gene which contains at least one such cis-acting nucleic acid sequence, which occurs during the production of mRNA of the gene, dependent upon activation of a trans-acting factor which is an RNA-activated protein kinase capable of phosphorylating the α-subunit of eukaryotic initiation factor 2 (eIF2α).

In specific embodiments the RNA-activated protein kinase is the RNA-activated protein kinase (PKR).

In a preferred embodiment the cis-acting nucleic acid sequence of the invention is derived from the 3' untranslated region of the human tumor necrosis factor α gene (TNF-α3'-UTR).

In especially preferred embodiments the cis-acting nucleic acid sequence of the invention comprises the nucleotide sequence substantially as denoted by SEQ ID NO:1. The invention also relates to biologically functional fragments, derivatives, mutants and homologues of this sequence and to nucleotide sequences which can hybridize with complementary nucleotide sequences of SEQ ID NO:1 and the biologically functional fragments, derivatives, mutants and homologues thereof.

In a most preferred embodiment the cis-acting nucleic acid sequence of the invention comprises SEQ ID NO:2 and biologically functional fragments, derivatives, mutants and homologues thereof.

SEQ ID NO:1 and SEQ ID NO:2 are provided, hereinafter, in Table 1.

The cis-acting nucleic acid sequences according to the invention are capable of rendering the removal of intron/s from a precursor transcript encoded by a gene which harbors at least one such cis-acting nucleic acid sequence, which occurs during the production of mRNA of the gene, dependent upon activation of a trans-acting factor which is an RNA-activated protein kinase capable of phosphorylating the α-subunit of eukaryotic initiation factor 2 (eIF2α). The gene can be any gene of interest, including genes having a therapeutic, industrial, agricultural or any other commercial value or genes encoding proteins which are of therapeutic, industrial, agricultural or of any other commercial value.

In a further aspect, the invention relates to a DNA construct comprising a gene which contains at least one intron; a cis-acting nucleotide sequence which is capable of rendering the removal of intron/s from a precursor transcript encoded by said gene, which gene includes at least one such cis-acting nucleotide sequence, occurring during the production of mRNA of said gene, dependent upon activation of a trans-acting factor, said trans-acting factor being an RNA-activated protein kinase which is capable of phosphorylating the α-subunit of eukaryotic initiation factor 2, operably linked to said gene; and optionally further comprising additional control, promoting and/or regulatory elements.

In particular embodiments, said cis-acting nucleotide sequence in the DNA construct according to the invention comprises the nucleotide sequence substantially as denoted by SEQ ID NO:1 or by SEQ ID NO:2, or biologically functional fragments, derivatives, mutants and homologues of the nucleotide sequence substantially as denoted by SEQ ID NO:1 or by SEQ ID NO:2, or a nucleotide sequence whose complementary sequence hybridizes, under conditions which allow for such hybridization to occur, with the said nucleotide sequences.

In the DNA constructs according to the invention, said gene is preferably a gene which encodes a protein is selected from the group consisting of enzymes, hormones, growth factors, cytokines, structural proteins and industrially or agriculturally applicable proteins, or is itself a therapeutic product, an agricultural product, or an industrially applicable product.

In the DNA constructs according to the invention said nucleotide sequence can be contained within an exon or within an intron of said gene.

In a further aspect, the invention relates to a vector comprising the cis-acting nucleotide sequence or a DNA construct according to the invention and a suitable DNA carrier, capable of transfecting a host cell with said cis-acting nucleotide sequence.

In an additional aspect, the invention relates to a host cell transfected with a cis-acting nucleotide sequence or with a DNA construct according to the invention, capable of expressing substantial amounts of said gene. The transfected host cells in accordance with the invention are preferably eukaryotic or yeast cells.

In addition, the invention relates to a transgenic animal carrying in its genome a cis-acting nucleotide sequence or a DNA construct according to the invention, which is capable of expressing substantial amounts of said gene.

Additionally, the invention relates to a transgenic plant carrying in its genome a cis-acting nucleotide sequence or a DNA construct according to the invention, which is capable of expressing substantial amounts of said gene.

Furthermore, the invention relates to methods of regulating gene expression at the mRNA splicing level by (a) providing a cis-acting nucleotide sequence which is capable of rendering the removal of intron/s from a precursor transcript encoded by a gene which contains at least one intron dependent upon activation of a trans-acting factor, said trans-acting factor being an RNA-activated protein kinase which is capable of phosphorylating the α-subunit of eukaryotic initiation factor 2; (b) operably linking said cis-acting nucleotide sequence to said gene to give a DNA construct; (c) optionally combining the construct thus obtained with a suitable DNA carrier and optionally operably linking the same to suitable additional expression control, promoting and/or regulatory elements to give a transfection vector which is capable of transfecting a host cell; (d) transfecting a host cell with a cis-acting nucleotide sequence of the invention, or with a DNA construct of the invention or with the transfection vector, wherein the host cell is capable of expressing an RNA-activated protein kinase which is capable of phosphorylating the α-subunit of eukaryotic initiation factor 2; (e) to give a transfected host cell capable of expressing said gene in substantial amounts, in which the expression and/or activity of the RNA-activated eIF2α kinase in said host cell is modulated.

The present invention also encompasses various methods for treating an individual suffering an acquired or hereditary pathological disorder in which a therapeutic product is not made by said individual, or made is in abnormally low amounts or in a defective form or is made in essentially normal amount to be increased by providing a DNA construct or a vector according to the invention in which said gene encodes said therapeutic product and transfecting cells of said individual with the provided DNA construct or vector, whereby cells of said individual become capable of expressing said gene.

Pharmaceutical compositions comprising as active ingredient a therapeutically effective amount of a cis-acting nucleotide sequence, a DNA construct, a transfection vector or transfected host cells according to the invention are also within ambit of the present invention.

In yet a further embodiment, the invention relates to methods of producing recombinant proteins by the transfected host cells, transgenic animals or transgenic plants in accordance with the invention.

BRIEF DESCRIPTION OF THE DRAWINGS

FIG. 1 Gene constructs used

Figure 2A:
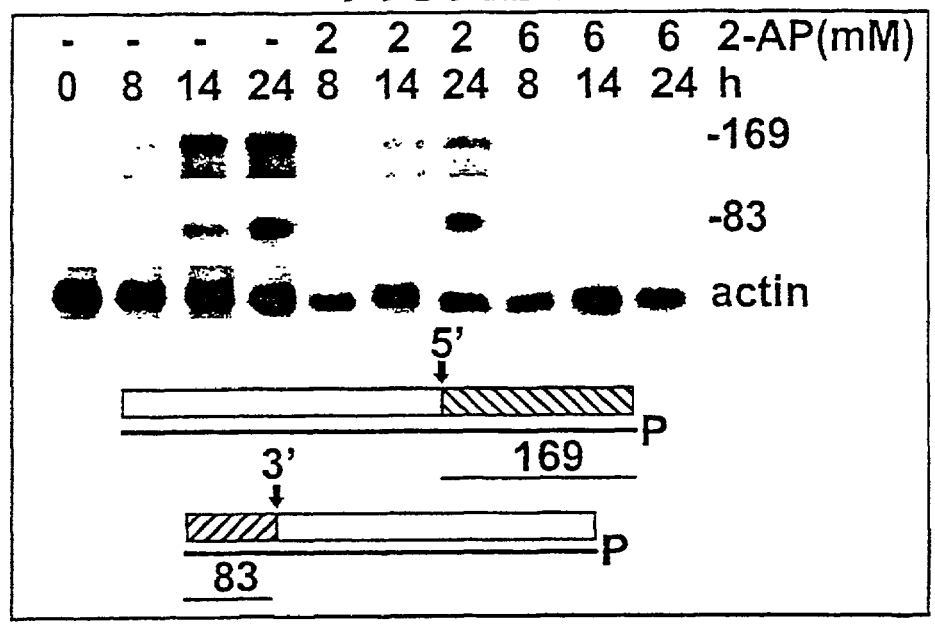

Introns are white boxes; ex, exon; 3'UTRα, TNF-α3'-UTR; $A_n$, polyadenylation and cleavage site of TNF-α gene (α), TNF-β gene (β) or SV40; nd, not determined; 5'α, 3'α and 3'β are defined in the text. E, EcoRI site; P, PstI site.

FIGS. 2A–2F TNF-α3'-UTR sequences are needed for inhibition of mRNA splicing by 2-AP BHK-21 cells were transfected with pTNF-α (A, B–D), p5'αCAT (E) or pTNF-α(Δ3'UTR) DNA (F) and co-transfected with pSV$_2$CAT DNA (B, F). 2-AP was present from time of transfection at the concentrations shown (A), or from 18 h thereafter at 10 mM (B–F). Cell viability remained constant. Total RNA was isolated at times shown after transfection and subjected to RNase protection analysis with $^{32}$P-labeled TNF-α antisense RNA probes P (A, B, F) to quantitate correctly initiated TNF-α RNA (A: 169-nt band), TNF-α RNA carrying a correct 3' end (A: 83-nt band), TNF-α precursor transcripts (B, F: 700-nt band) or spliced RNA (B, F: 341-nt band). In (B), upper autoradiogram shows a higher exposure of 700-nt band. Autoradiogram of (B) was subjected to densitometry; intensity of 700-nt band (C) and 341-nt band (D), expressed in the absence (○, □) or presence of 2-AP (●,■), is plotted. In B, E and F, CAT mRNA protects 250 nt of probe. In A and E, α-actin probe detects a 215-nt portion of mRNA. In autoradiograms A and E, left lane shows untransfected cells and in F, cells transfected with pSV$_2$CAT DNA alone.

FIGS. 3A–3E TNF-α3'-UTR sequences suffice to confer splicing control by 2-AP

BHK-21 cells were transfected with pTNF-β (A, B), pTNF-β(3'UTR-α) (C, D) or pTNF-α(3'UTR-β) DNA (E) and co-transfected with pSV$_2$CAT DNA. 2-AP was present from 12 (A, B) or 16 h after transfection (C–E) and CHX from 16 h (C, D). Cell viability remained constant. Total RNA was isolated at times shown and subjected to RNase protection analysis with $^{32}$P-labeled antisense TNF-β intron 3/exon 4 RNA probe P to quantitate precursor transcripts (637-nt band) and spliced RNA (571-nt band) (A, C) or TNF-β exon 1/exon 2/exon 3/intron 3 probe P to quantitate precursor transcripts (324-, 275- and 169-nt bands) and spliced RNA (214-nt band) (B, D). M, size marker. In E, TNF-α precursor transcripts (700-nt band) and spliced RNA (341-nt band) were analyzed as for FIG. 2B; upper autoradiogram shows a higher exposure of 700-nt band. CAT mRNA protects 250 nt of probe.

FIGS. 4A–4D The TNF-α3'-UTR harbors an RNA element that activates PKR

TNF-α3'-UTR DNA constructs (A) or TNF-β3'-UTR DNA were used to generate T7 RNA transcripts that at the concentrations shown were incubated with rabbit reticulocyte ribosomal fraction and [γ-$^{32}$P]ATP; dsRNA (polyI:polyC) served as control (B). Autoradiogram of protein gel (B) was quantitated to yield, for each TNF RNA at 0.05 ng/ml, molar specific phosphorylation activity for PKR (C). In (D), dsRNA or purified 3'UTR-αEP T7 transcript were incubated and analyzed as in (B), with 2-AP present at the indicated concentrations (in mM).

FIG. 5 Nuclease sensitivity mapping of TNF-α3'UTR-αEP RNA 5' End-labeled 3'UTR-αEP RNA was digested with T1, U2 or V1 nuclease directly to assay structure (str) (c, without nuclease) and, for T1 and U2, also after denaturation at 50° C. in 7 M urea (seq). Nucleotide ladder was generated by alkaline hydrolysis (OH). Autoradiogram of sequencing gel is shown (FIG. 5A). Stem and loop regions relate to secondary structure at right, showing sites of nuclease attack, based on multiple analyses. GGGC is from plasmid. 2-APRE is the 2-AP response element (SEQ ID NO. 7) (FIG. 5B). Phylogenetic conservation of sequences is shown for *Homo sapiens* (human) (SEQ ID NO. 8), Sus scrofa (wild boar) (SEQ ID NO. 9), *Oryctolagus cuniculus* (rabbit) (SEQ ID NO. 10), *Bos taurus* (bull) (SEQ ID NO.11) and *Capra hircus* (goat) (SEQ ID NO.12) (Fig. 5C).

FIG. 6 The 2-APRE renders splicing of TNF-α mRNA dependent on activation of PKR

BHK-21 cells were transfected with pTNF-α(3'UTR-αEP) or pTNF-α(Δ3'UTR) and where indicated, co-transfected with pPKRΔ6. pSV$_2$CAT DNA was co-transfected in each case. 2-AP was added at 20 h after transfection where shown. Total RNA was analyzed as for FIG. 2B to quantitate TNF-α precursor transcripts (700 nt) and spliced RNA (341 nt). CAT mRNA protects 250 nt of probe.

Figure 7A:
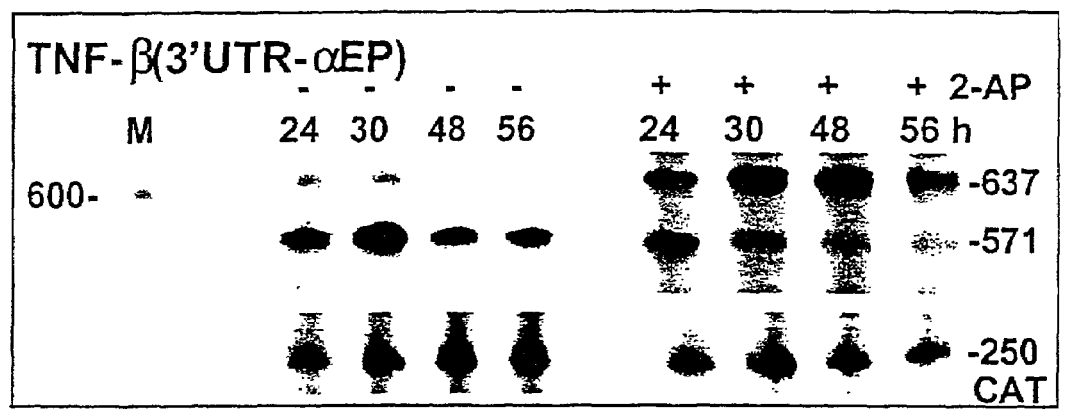
Figure 7B:
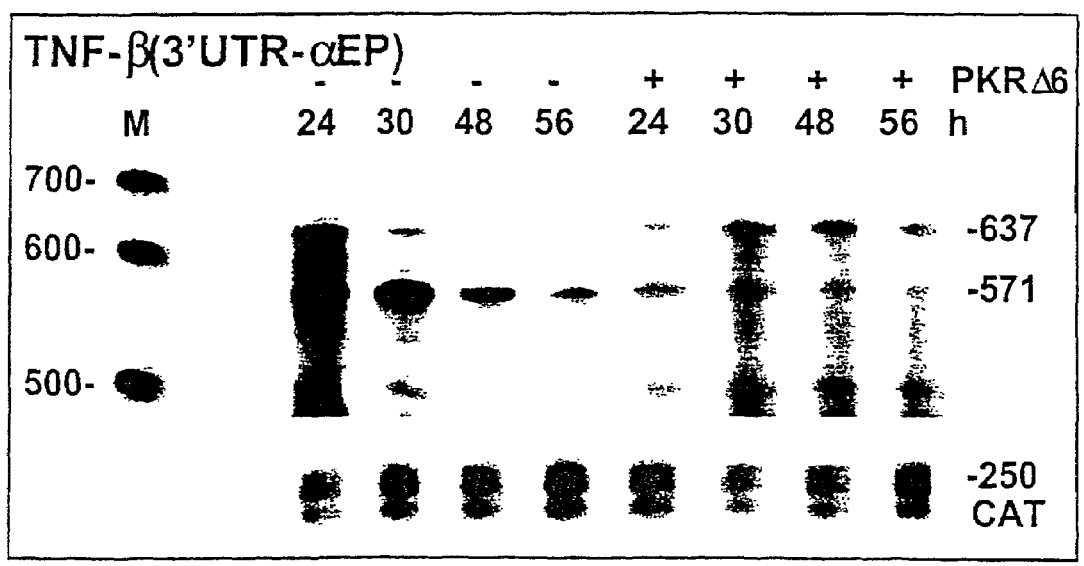
Figure 7C:
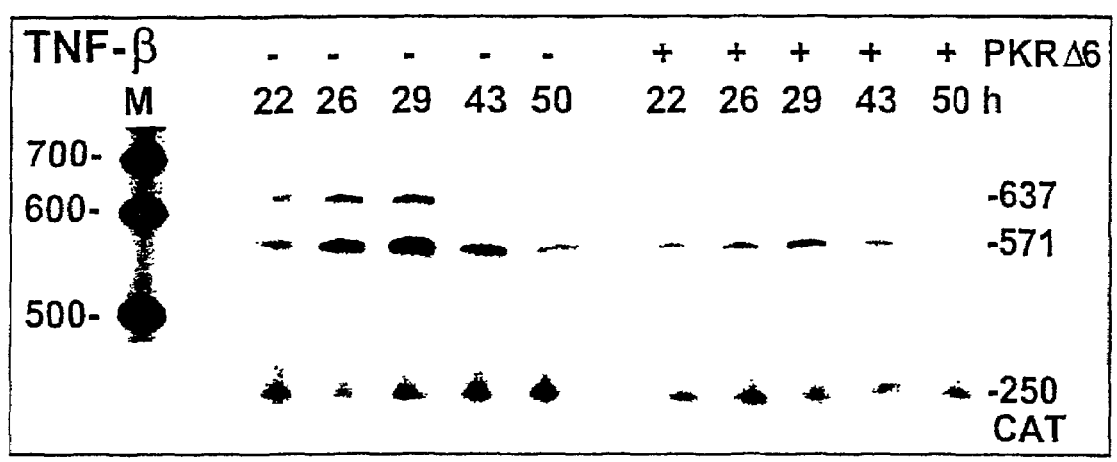

FIG. 7A–7C The TNF-α2-APRE renders splicing of TNF-β mRNA dependent on activation of PKR BHK-21 cells were transfected with pTNF-β(3'UTR-αEP) (A, B) or pTNF-β (C) and where indicated, co-transfected with pPKRΔ6. pSV$_2$CAT DNA was co-transfected in each case. In (A), 2-AP was added at 20 h after transfection. Total RNA was analyzed as for FIG. 3A to quantitate TNF-α precursor transcripts (637 nt) and spliced RNA (571 nt). M, size marker. CAT mRNA protects 250 nt of probe.

Figure 8:
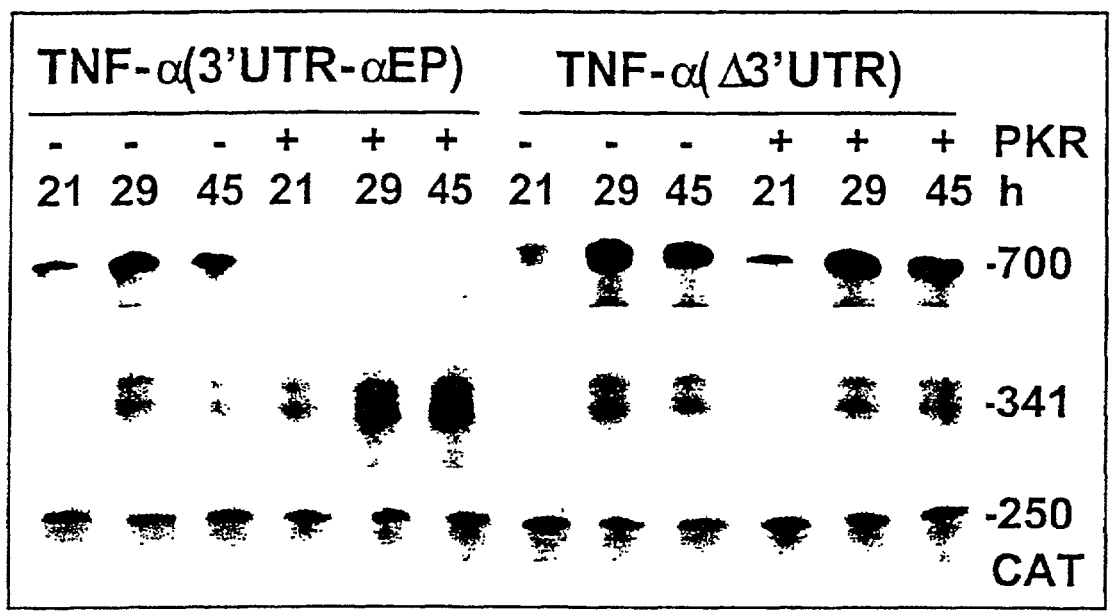

FIG. 8 The 2-APRE renders splicing of TNF-α mRNA dependent on activation of PKR.

BHK-21 cells were transfected with pTNF-α(3'UTR-αEP) or pTNF-α(Δ3'UTR) and where indicated, co-transfected with pPKR. pSV$_2$CAT DNA was co-transfected in each case. Total RNA was analyzed as for FIG. 2B to quantitate TNF-α precursor transcripts (700 nt) and spliced RNA (341 nt); upper autoradiogram shows a higher exposure of 700-nt band. CAT mRNA protects 250 nt of probe.

DETAILED DESCRIPTION OF PREFERRED EMBODIMENTS

In search for a regulatory element which could control expression at the mRNA splicing level, and could thus form the basis for improved design of eukaryotic expression vectors, improve the basal yield of expression vectors and enable implementing a novel mode of regulation of gene expression at the level of mRNA splicing, the inventors have surprisingly discovered that the human TNF-α gene is so regulated, i.e. it is regulated at the level of splicing of mRNA.

As will be demonstrated in the following Examples, the inventors have shown that the 3' untranslated region of the human TNF-α gene (TNF-α 3'-UTR) contains a cis-acting element that renders splicing of precursor transcripts encoded by this gene dependent on the activation of PKR. Insertion of this element, or functional derivatives thereof, for example a minimal functional portion of the TNF-α3'-UTR, designated herein 2-APRE (2-AP response element), into another gene renders splicing of precursor transcripts encoded by that other gene sensitive to the level of PKR activity which can be manipulated, for example, by the eIF2α kinase inhibitor, 2-AP, or by co-expression of a transdominant-negative mutant of PKR. Thus, PKR responds as trans-acting factor to the 2-APRE. 2-APRE-encoded RNA forms a stable, 17-bp stem-loop structure and strongly activates PKR in vitro, inducing eIF2α phosphorylation.

Splicing of TNF-α precursor transcripts into mature mRNA molecules is blocked in intact cells by 2-aminopurine (2-AP) [13]. Removal of most of the 3' untranslated region of the TNF-α gene (3'-UTR) led to loss of splicing regulation by 2-AP and the TNF-α3'-UTR is sufficient to render splicing at multiple introns sensitive to 2-AP. The 2-APRE was mapped into a 104 nt region in the 3'-UTR, located well upstream of the AU-rich mRNA instability sequence that was shown to repress TNF translation [14]. By replacing 3'-UTR sequences in a heterologous gene with TNF-α3'-UTR sequences containing the 2-APRE, a chimeric gene was created whose expression had become sensitive to inhibition by 2-AP at splicing, demonstrating a transcript-independent function of the 2-APRE element. The observed 2-AP sensitivity of TNF-α pre-mRNA splicing suggested that this effect is mediated through the PKR protein, the role of which has been extensively discussed above.

The inventors have thus discovered a novel regulatory expression element, the 2-APRE, which can act as a regulatory expression element at the mRNA splicing level and can be employed for increasing as well as regulating expression of genes. The DNA sequence encoding the 2-APRE element is denoted herein as SEQ ID NO:1.

Therefore, the invention relates to a cis-acting nucleic acid sequence which is capable of rendering the removal of intron/s from a precursor transcript encoded by a gene, which gene harbors at least one such cis-acting nucleic acid sequence, occurring during the production of mRNA of said gene, dependent upon activation of a trans-acting factor, said trans-acting factor being an RNA-activated protein kinase which is capable of phosphorylating the α-subunit of eukaryotic initiation factor 2.

In preferred embodiments the cis-acting nucleic sequence of the invention renders the removal of intron/s from said precursor transcripts dependent upon activation of RNA-activated protein kinase (PKR).

In specific embodiments of the invention, the cis-acting nucleotide sequence is derived from the 3' untranslated region of the human tumor necrosis factor α gene (TNF-α3'-UTR).

Thus, a preferred cis-acting nucleotide sequence according to the invention comprises (a) the nucleotide sequence substantially as denoted by SEQ ID NO:1; or (b) biologically functional fragments, derivatives, mutants and homologues of the nucleotide sequence substantially as denoted by SEQ ID NO:1; or (c) a nucleotide sequence whose complementary nucleotide sequence hybridizes, under conditions which allow for such hybridization to occur, with the nucleotide sequences of (a) or (b).

A most preferred cis-acting nucleotide sequence according to the invention comprises (a) the nucleotide sequence substantially as denoted by SEQ ID NO:2; or (b) biologically functional fragments, derivatives, mutants and homologues of the nucleotide sequence substantially as denoted by SEQ ID NO:2; or (c) a nucleotide sequence whose complementary nucleotide sequence hybridizes, under conditions which allow for such hybridization to occur, with the nucleotide sequences of (a) or (b).

SEQ ID NO:1, SEQ ID NO:5, SEQ ID NO:2 and SEQ ID NO:6 are shown in the following Table 1.

sequence hybridizes, under conditions which allow for such hybridization to occur, with the nucleotide sequence denoted by SEQ ID NO:2 or with the biologically functional fragments, derivatives, mutants and homologues thereof.

TABLE 1

SEQ ID NO: 1

```
     GAATTCAAACTGGGGCCTCCAGAACTCACTGGGGCCTACAGCTTTGATCCCTGACATCTG
2817---------+---------+---------+---------+---------+---------+2876
     CTTAAGTTTGACCCCGGAGGTCTTGAGTGACCCCGGATGTCGAAACTAGGGACTGTAGAC

GAATCTGGAGACCAGGGAGCCTTTGGTTCTGGCCAGAATGCTGC
2877---------+---------+---------+---------+----2920
     CTTAGACCTCTGGTCCCTCGGAAACCAAGACCGGTCTTACGACG
```

SEQ ID NO: 2

```
     TCAAACTGGGGCCTCCAGAACTCACTGGGGCCTACAGCTTTGA
2821-----+---------+---------+---------+-------2863
     AGTTTGACCCCGGAGGTCTTGAGTGACCCCGGATGTCGAAACT
```

As shown in Example 7 and FIG. 5B, 3'UTR-αEP RNA forms a stable, 5'-proximal 48-nt stem-loop containing 17 base pairs (DG=−59 kJ at 30° C.). The DNA encoding this stem loop is denoted herein by SEQ ID NO:2.

The term "functional" as used herein is to be understood as any such sequence which would render the removal of introns from precursor mRNA transcripts encoded by a gene which harbors such sequences, dependent upon activation of a trans-acting factor which is an RNA-activated protein kinase capable of phosphorylating eIF2α.

In a further aspect the invention relates to a DNA construct comprising a gene which contains at least one intron; a cis-acting nucleotide sequence which is capable of rendering the removal of intron/s from a precursor transcript encoded by said gene, which gene includes at least one such cis-acting nucleotide sequence, occurring during the production of mRNA of said gene, dependent upon activation of a trans-acting factor, said trans-acting factor being an RNA-activated protein kinase which is capable of phosphorylating the α-subunit of eukaryotic initiation factor 2, operably linked to said gene; and optionally further comprises additional control, promoting and/or regulatory elements.

The control, promoting and/or regulatory elements are suitable transcription promoters, transcription enhancers and mRNA destabilizing elements, or any other suitable elements known to those skilled in the art.

In a specific embodiment, the cis-acting nucleotide sequence contained within a DNA construct of the invention comprises the nucleotide sequence substantially as denoted by SEQ ID NO:1; or biologically functional fragments, derivatives, mutants and homologues of the nucleotide sequence substantially as denoted by SEQ ID NO:1; or a nucleotide sequence whose complementary sequence hybridizes, under conditions which allow for such hybridization to occur, with the nucleotide sequences denoted by SEQ ID NO:1 or with the biologically functional fragments, derivatives, mutants and homologues thereof.

In a particularly preferred embodiment the cis-acting nucleotide sequence contained within the DNA construct of the invention comprises the nucleotide sequence substantially as denoted by SEQ ID NO:2; or biologically functional fragments, derivatives, mutants and homologues of the nucleotide sequence substantially as denoted by SEQ ID NO:2; or a nucleotide sequence whose complementary The cis-acting nucleotide sequence comprised in the DNA constructs of the invention may be contained within an exon or within an intron of the gene.

In the DNA construct of the invention said gene may encode a protein selected from the group consisting of enzymes, hormones, growth factors, cytokines, structural proteins and industrially or agriculturally applicable proteins, or the gene is itself a therapeutic product, an agricultural product, or an industrially applicable.

Specific DNA constructs according to the invention are such in which the gene is the human TNF-α gene. Examples for such constructs are the plasmid pTNF-α (FIG. 1C) and the plasmid pTNF-α(3'UTR-αEP) (FIG. 1I), in both of which the cis-acting element is contained within an exon of the gene. The cis-acting element may also be contained within an intron of said gene, as in, for example, the plasmid pTNF-α(Δ3'UTR)i3EP (FIG. 1K).

Other specific DNA constructs are such in which the gene is the human TNF-β gene. Examples for these constructs are the plasmid pTNF-β(3'UTR-α) (FIG. 1F) and the plasmid pTNF-β(3'UTR-αEP) (FIG. 1J), in both of which the cis-acting element is contained within an exon of the gene.

In a further aspect, the invention relates to a transfection vector comprising the cis-acting element of the invention, or functional fragments, derivatives, homologues or mutants thereof, optionally operably linked to suitable additional control, promoting and/or regulatory sequences. The vectors of the invention are designed to facilitate the introduction of the cis-acting element into a host cell.

The vectors may contain suitable additional control, promoting and/or regulatory sequences of cellular and/or viral origin. The invention relates also to host cells transfected with a gene of interest operably linked to the cis-acting element of the invention, or with the cis-acting element of the invention itself, and to their various uses.

Specifically, the invention relates to a host cell transfected with a DNA construct or an expression vector according to the invention. Alternatively, the host cell may be transfected with DNA encoding a cis-acting element according to the invention itself. Host cells according to the invention can also be cells only transfected with the cis-acting nucleotide sequence of the invention.

The host cells according to the invention may be eukaryotic or yeast cells. Examples of eukaryotic cells are, inter alia, mammalian hemopoietic cells, fibroblasts, epithelial cells, or lymphocytes.

Specific host cells which may be transfected are the baby hamster kidney (BHK-21) cell line or the Chinese hamster ovary (CHO) cell line.

With the development of gene transfer techniques that allow the generation of transgenic animals came the possibility of producing animal bioreactors as an alternative strategy to cell culture systems for protein production [25]. For instance, protein secretion in the milk of large mammals could provide a cost effective route for the production of large amounts of valuable proteins. As yet this technology is still in development and needs optimization, and there is a general requirement for methods to improve productivity. The cis-acting nucleotide sequences according to the invention may help attain this goal by improved regulation of the expression of a desired protein.

Thus, the invention also relates to a transgenic animal which carries in its genome a cis-acting nucleotide sequence or DNA construct in accordance with the invention, which transgenic animal is capable of expressing substantial amounts of protein encoded by said gene.

The transgenic animals of the invention may be used in a method of producing recombinant enzymes, hormones, growth factors, cytokines, structural proteins or other industrially or agriculturally applicable proteins, also encompassed by the present invention, which process comprises the steps of (a) providing a transgenic animal transformed with a DNA construct according to the invention, in which said gene encodes such enzyme, hormone, growth factor, cytokine, structural protein or another industrially or agriculturally applicable protein, said transgenic animal being capable of expressing said gene in substantial amounts; (b) growing the transgenic animal provided in (a) under suitable conditions to allow the said gene to be expressed; and (c) isolating the protein encoded by said gene from said animal, or from an egg or body secretion thereof. Techniques in which the gene is expressed, for example, in cattle's milk and chicken eggs may be used, and the desired protein encoded by the gene isolated.

Regulated expression could be achieved by several routes. To date, transcriptional regulation has received most attention [1–4], while little effort has been directed at improving efficiency of pre-mRNA processing. In the broader context, mechanisms allowing the regulation of RNA processing would assist gene transfer, be it into cell lines, the germline or somatic tissues. Transgenic animals, provide an appropriate model for testing gene therapy constructs, where an ability to regulate expression is of paramount importance.

The present discovery of the cis-acting element in the human TNF-α3'-UTR that renders splicing of TNF-α mRNA sensitive to inhibition by 2-AP, provides a unique and novel tool for bringing expression of a desired gene under the control of this mechanism. Such regulation can be implemented by introducing the cis-acting element into expression vectors and generating cell lines in which the expression of PKR can be manipulated. The exonic cis-acting element from the TNF-α gene of this invention, is a portable element that confers splicing control. Since upon transport into the cytosol, however, localized activation of PKR by the cis-acting element residing in resulting mature mRNA may tend to reduce its translation efficiency through phosphorylation of eIF-2, the advantage gained from control of splicing may thus be offset by a loss in translation efficiency. To solve this problem, important for applications in biotechnology, the cis-acting element can be moved from the TNF-α3'-UTR into an intron of this gene. After first activating the splicing mechanism in cis, the intronic cis-acting element itself will now be spliced out of the mRNA, yielding a cis-acting element-free mRNA that should no longer activate PKR through this element during translation.

Genes rendered sensitive to cis-acting element-mediated splicing control by insertion of the cis-acting element can be cotransfected with a negative dominant mutant of PKR, for example, PKRΔ6, to inhibit or modulate PKR-dependent splicing in transfected cells. Further, cotransfection with a constitutively expressed adenovirus VA RNA construct [34] can be used as tool to inhibit or reduce activation of PKR. Further, cotransfection with a constitutively expressed vaccinia virus E3L, K3L construct [62,63] can be used as tool to inhibit or reduce activation of PKR. A regulated expression system based on the regulation of TNF-α expression at the level of splicing in such a way that it can be controlled by low molecular weight compounds in the medium can be designed. As for most regulated expression systems, this will depend upon the presence of two distinct components: the target element in the expression vector (for example, the human TNF-α cis-acting element) and a regulated effector provided by manipulating the expression and/or activity of RNA-activated protein kinase capable of phosphorylating the α-subunit of eukaryotic translation initiation factor 2. Such a system may later be combined with already existing vectors in which expression is regulated at the level of transcription or translation.

The cis-acting element from the TNF-α gene element can be chosen initially for splicing control. This element, preferably in the intronic form, may be integrated into vectors having any convenient reporter genes for qualitative and quantitative testing. The cis-acting element may be integrated at different positions, 3' or 5' to the reading frame of the reporter gene, in order to assess its function in splicing regulation as well as possible side effects on transcription yield, mRNA half-life, and translation yield. Reporter genes to optimize the construct can be firefly luciferase and green fluorescent protein mutants. Both reporters can be integrated in one test vector, either as a bicistronic construct or, preferentially, as a bifunctional fusion protein. The promoter of the resulting vector construct containing the gene to be expressed will be constitutive with respect to manipulation of cells and the application of regulating compounds to be described below.

The trans-acting regulator presently implicated for the cis-acting element is RNA-activated protein kinase capable of phosphorylating α-subunit of eukaryotic translation initiation factor 2. Downregulation of RNA-activated protein kinase capable of phosphorylating the subunit of eukaryotic translation initiation factor 2 should reduce splicing, while overexpression of said kinase should increase it. Although overexpression of RNA-activated protein kinase capable of phosphorylating the α-subunit of eukaryotic translation initiation factor 2 occurs, for example, in interferon-treated cells, the enzyme remains inactive as long as viral dsRNA is lacking, thus allowing translation to proceed unabated and cells to grow normally. As an alternative to obtaining a functional self-eliminating cis-acting element, is nuclear targeting of RNA-activated protein kinase capable of phosphorylating the α-subunit of eukaryotic translation initiation factor 2 through a nuclear localization signal.

Regulating the activity of RNA-activated protein kinase capable of phosphorylating the α-subunit of eukaryotic translation initiation factor 2 may be achieved by the construction of fusion proteins between an RNA-activated protein kinase capable of phosphorylating the α-subunit of eukaryotic translation initiation factor 2 and specific protein receptor elements, for example hormones receptor elements. In many examples, it was shown before that such fusion proteins are fully dependent on the respective protein (in the case of hormones, e.g. progesterone, estradiol, or tamoxifen). Both wild type PKR and the negative dominant mutant PKRΔ6 may be considered. The function of these fusion proteins in dependence on the protein (e.g. steroid hormone) can be tested by examining autophosphorylation of the PKR fusion protein or its targets, endogenous PKR or eIF-2. Furthermore, this regulation may be tested with respect to reporter gene expression of cotransfected splicing vector containing the cis-acting element.

As an alternative to regulating the activity of an RNA-activated protein kinase capable of phosphorylating the α-subunit of eukaryotic translation initiation factor 2, its expression can be controlled by use of the TET-off system [7]. Transactivator-containing cells can be supertransfected with the PKR gene under control of the tetracycline-dependent promoter. Thus, in the presence of tetracycline the promoter should be off and in its absence, overproduction of PKR or a transdominant-negative mutant, for example, PKRΔ6 should take place (E3L, K3L, VA or Eber RNA).

The invention will now be described with more detail on hand of the following Examples, which are illustrative only and do not limit the scope of the invention, only defined by the appended claims.

EXAMPLES

DNA Constructs for Transfection p5'CAT was constructed by subcloning a filled in 821-bp EcoRI-Sau3AI fragment containing TNF-α upstream regulatory sequences, the 151-bp 5'-UTR and the first 6 codons, into the filled in HindIII site of pSV$_{40}$CAT which lacks the SV40 promoter/enhancer [47]. p5'CAT(3'-UTR-α) was constructed by subcloning a 823-bp filled in EcoRI-EcoRI TNF-α gene fragment comprised of 573 3'-terminal bp of the 3'-UTR, the polyadenylation site and downstream sequences, into the HpaI site downstream of the CAT coding region in p5'CAT. pTNF-α contains the entire human TNF-α gene, including upstream regulatory sequences [48], in pUC13pML. pTNF-(Δ3'UTR), a construct containing the entire TNF-α gene but lacking 573 3'-terminal bp of the 3'-UTR, was made by digesting pTNF-α with EcoRI and subcloning the 2,796-bp 5'-terminal TNF-α gene fragment into pBS (Stratagene). pTNF-β, a construct containing the entire human TNF-β gene, including 572 bp upstream of the transcription start site and 250 bp downstream from the 3'-UTR, was constructed by digesting cosmid vector 019A containing 35 Kbp of the MHC class II locus with BamHI and SacI and subcloning the resulting 2,858-bp TNF-β genomic fragment into pBS. In pTNF-β(3'UTR-α), the TNF-β gene is truncated 160 bp into the 3'-UTR and abutted to a 823-bp EcoRI-EcoRI TNF-α gene fragment comprised of 573 3'-terminal bp of the 3'-UTR, the polyadenylation site and downstream sequences; the construct was generated by digesting cosmid vector 019A with EcoRI and joining, in pBS, the resulting 2,384-bp TNF-β gene fragment to the first fragment. In the reciprocal construct, pTNF-α(3'UTR-β), the TNF-α gene in pTNF-α was truncated 219 bp into the 3'-UTR by digestion with EcoRI and joined to a 572-bp EcoRI-PstI TNF-β gene fragment comprised of 389 3'-terminal bp of the 3'-UTR, the polyadenylation site and downstream sequences.

pTNF-α(3'UTR-αEP) was constructed in pTNF-α by joining a 2,894-bp SmaI-PstI TNF-α gene fragment to a 333-bp SphI-SphI TNF-β gene fragment containing 153 terminal bp of the 3'-UTR, the polyadenylation site and downstream sequences. To this end, a 3,231-bp SmaI-SspI TNF-α gene fragment was first inserted into the SmaI site of pBS and a 333-bp SphI-SphI TNF-β gene fragment inserted into the downstream SphI site. PstI digestion and self-ligation then joined the TNF-α gene, truncated at the PstI site in the 3'-UTR, to this TNF-β gene fragment, with an intervening 6-bp PstI-SphI sequence from pBS. pTNF-β(3'UTR-αEP) was constructed from pTNF-α(3'UTR-αEP) by digestion with EcoRI to remove the TNF-α gene up to the EcoRI site in the 3'-UTR and its replacement with a 2,139-bp EcoRI-EcoRI TNF-β gene fragment from pTNF-β. pPKRΔ6 contains the human PKR gene having a deletion of amino acids 361–366, under the CMV promoter [20].

pTNF-α(Δ3'UTR-i3EP) was constructed by joining SphI-digested pTKF-α(Δ3'UTR) DNA to the 333-bp SphI-SphI TNF-β gene fragment described above which is comprised of 153 terminal bp of the 3'-UTR, the polyadenylation site, and downstream sequences. This plasmid was then digested with XhoI which cuts uniquely inside TNF-α intron 3. A 2-APRE DNA fragment abutted by XhoI restriction sites was then inserted into this site. The 2-APRE DNA fragment was obtained by polymerase chain reaction using pTNF-α DNA as template and two synthetic DNA primers of sequences 5'-CCGCTCGAGAATTCAAACTGGGGC-CTCC-3' (SEQ ID NO: 3) and 5'-CCGCTCGAGTGCAG-CATTCTGGCCAGAACC-3' (SEQ ID NO:4) as 5' and 3' primers, respectively; the DNA product was digested with XhoI before ligation. Orientation of the 2-APRE insert in pTNF-α(Δ3'UTR-i3EP) was determined by analysis of DNA fragments generated upon PvuII/PstI digestion.

Cell Culture

BHK-21 cells were grown in DMEM medium supplemented with 2 mM glutamine, 40 mM NaHCO$_3$, 10 mM Hepes, pH 7.3, 100 mg/ml of penicillin and streptomycin, 10 mg/ml nystatin and 10% fetal calf serum. 2-AP (Sigma) was added at 10 mM unless otherwise indicated. To prepare a stock solution of 0.15 M, 2-AP was dissolved in phosphate-buffered saline by heating at 70° C. for 10 min. CHX (Sigma) was added at 20 mg/ml.

Transfection

In the experiments of FIGS. 2 and 3, monolayers of BHK-21 cells were seeded at a density of 1–2×10$^6$ cells/8-cm Petri dish and grown overnight; 4 h before cotransfection, culture medium was replaced. A mixture of 10 mg of test DNA construct and 4 mg salmon sperm DNA carrier, and, when included, 2 mg pSV$_2$CAT DNA [47], was permeated into cells by the calcium phosphate-DNA coprecipitation technique. After 12–18 h, culture medium was replaced with fresh medium prewarmed to 37° C. In the experiments of FIGS. 6 and 7, LipofectAmine (Life Technologies) was employed following instructions of the supplier, using 1 mg of each DNA for transfection.

Hybridization Probes

Figure 2B:
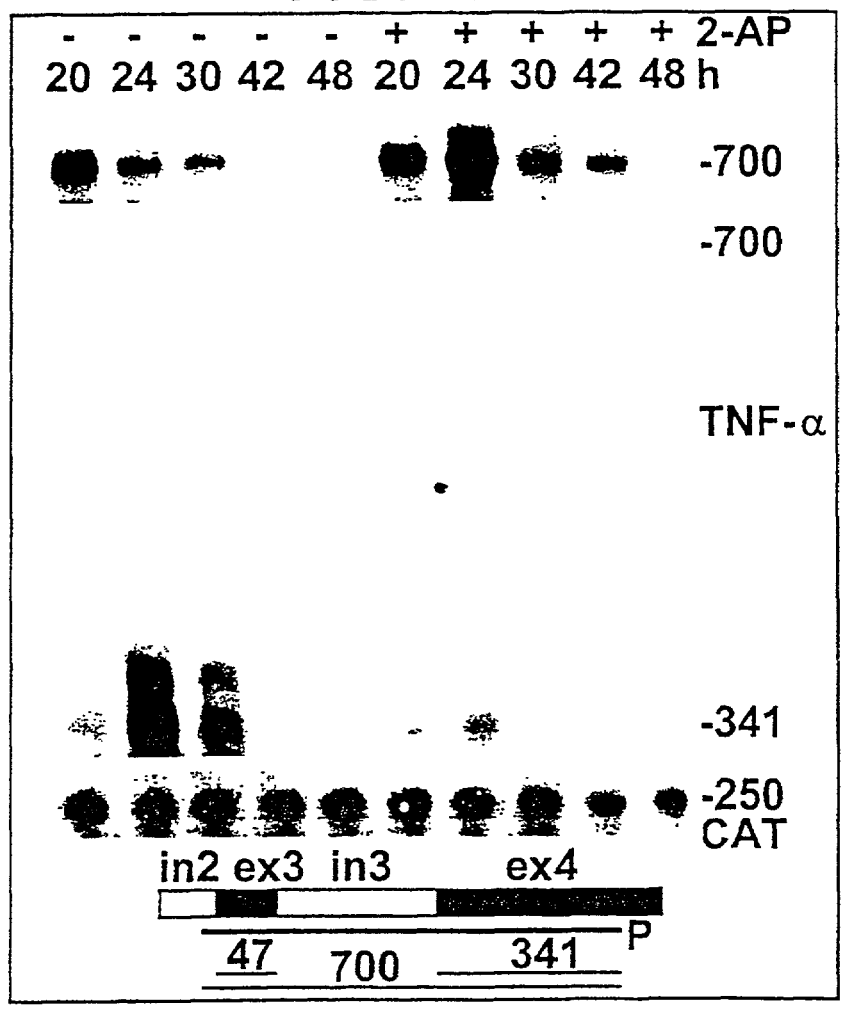
Figure 2C:
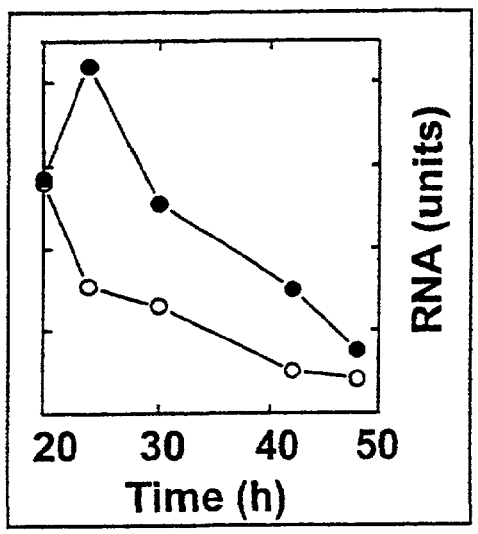
Figure 2D:
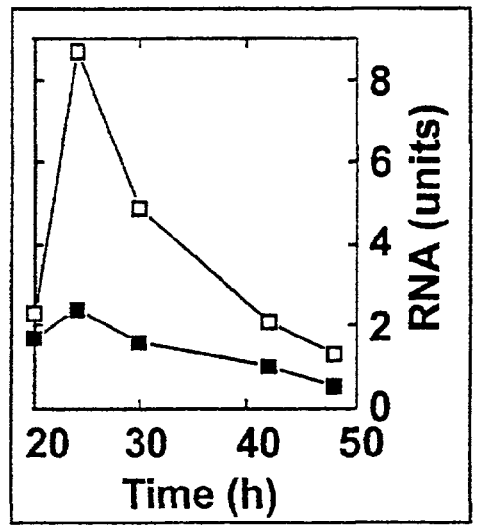
Figure 2E:
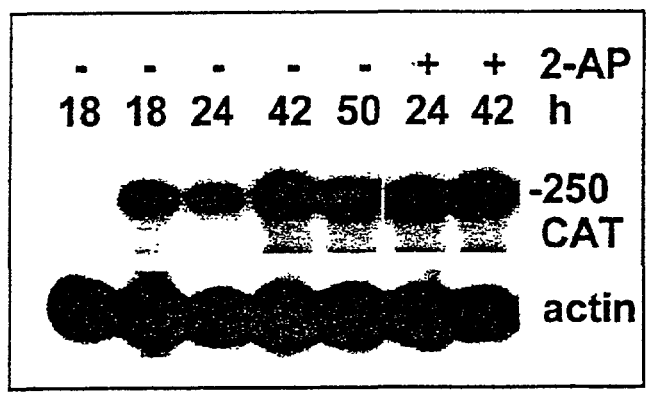
Figure 3A:
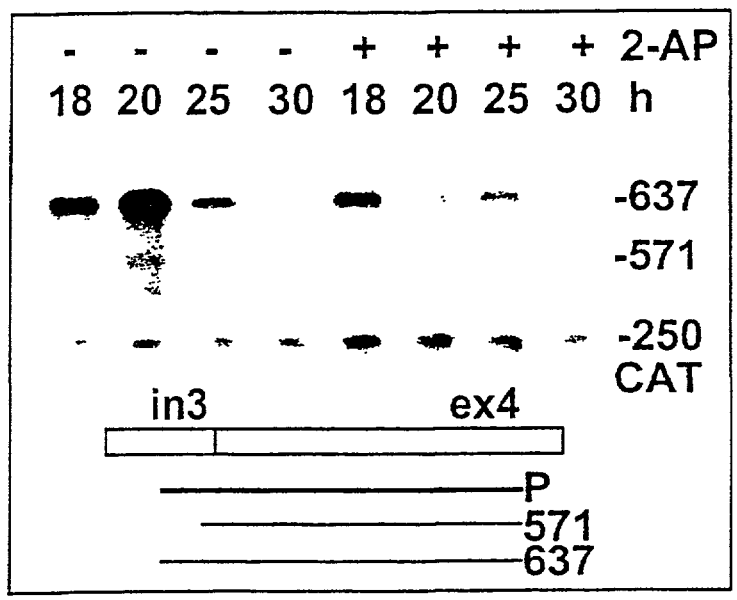
Figure 3B:
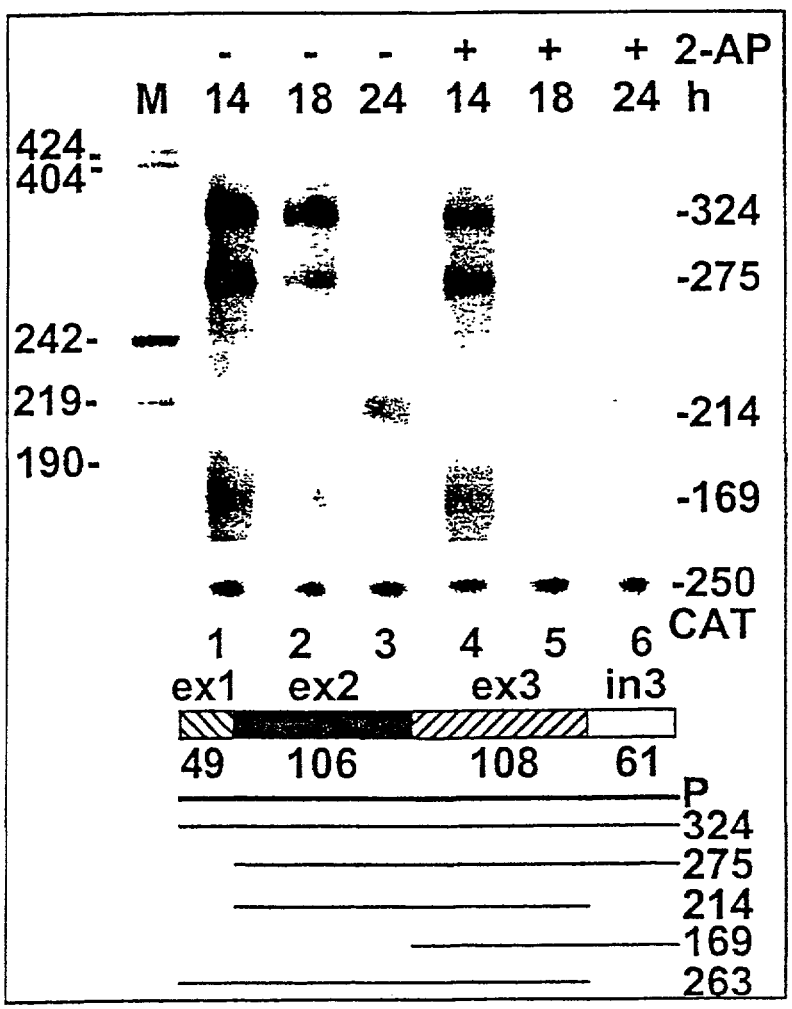

For RNase protection analysis, DNA was subcloned in pBS (Stratagene) under the T3 or T7 promoter and transcribed using [a-$^{32}$P]UTP to generate labeled anti-sense RNA transcripts. A TNF-α RNA probe (map: FIG. 2A) was generated from a 821-bp EcoRI-Sau3AI fragment containing the 5'-flank, 151 -bp 5'-UTR, and first 6 codons. A second TNF-α RNA probe was generated from a 823-bp EcoRI-EcoRI 3'-UTR fragment from which a 5'-terminal fragment was removed by BstEII digestion, leaving 83 3'-terminal bp of the 3'-UTR and 250 bp beyond the 3' cleavage site (map: FIG. 2A). A third TNF-α RNA probe (map: FIG. 2B) was generated from a 700-bp Sau3AI-Sau3AI fragment consisting of 10 bp of intron 2, exon 3, intron 3 and part of exon 4. A TNF-β probe was generated from a 637-bp Bsu36I-EcoRI DNA fragment, containing part of intron 3 and 571 bp of exon 4 (map: FIG. 3A). A second TNF-β RNA probe (map: FIG. 3B) was generated from a 324-bp EcoRI-Bsu36I DNA fragment, containing part of exon 1, exon 2, exon 3 and a portion of intron 3. A probe of 250-nt, generated from a HindIII-EcoRI fragment of the coding region of the CAT gene [47], was used to quantitate CAT mRNA. Intactness of RNA probes was assessed by polyacrylamide gel electrophoresis [13].

Ribonuclease Protection Analysis

Total RNA was isolated using guanidinium isothiocyanate/CsCl. RNase protection analysis with RNases A and T1 was performed using genomic TNF-α and TNF-β riboprobes and CAT or actin probes as described [13]. Protected RNA fragments were separated by electrophoresis in 5% polyacrylamide/8 M urea gels. Size markers in FIG. 3 were generated by MspI digestion of pGEM-3 DNA and filling in with [a-$^{32}$P]dCTP [12]. Size marker in FIG. 7 is a 100-bp DNA ladder (Fermentas) that was dephosphorylated and 5' end-labeled with [γ-$^{32}$P]ATP.

Activation of PKR by 3'-UTR Transcripts

A 823-bp EcoRI-EcoRI TNF-α gene fragment comprised of 573 3'-terminal bp of the 3'-UTR, the polyadenylation site and downstream sequences from pTNF-α was inserted into pBS under the T7 promoter. To obtain 3'-UTR sense transcripts, the DNA was digested with PstI (EP), NcoI (EN), AflIII (EA), SspI (ES) or XmnI (EX) and then transcribed in vitro. A 616-bp NcoI-EcoRI TNF-α gene fragment comprised of 366 3'-terminal bp of the 3'-UTR, the polyadenylation site and downstream sequences from pTNF-α was inserted into pBS under the T7 promoter. To obtain 3'-UTR sense transcripts, the DNA was digested with AflIII (NA) or XmnI (NX) and then transcribed in vitro. A 572-bp EcoRI-PstI TNF-β gene fragment comprised of 389 3'-terminal bp of the 3'-UTR, the polyadenylation site and downstream sequences from pTNF-β was inserted into pBS under the T7 promoter. To obtain 3'-UTR sense transcript, the DNA was digested with PstI and then transcribed in vitro. EP RNA transcript was purified by agarose gel electrophoresis, followed by chromatography on CF-11 cellulose, washing with ethanol and eluting with water as described [38]. Phosphorylation of PKR and eIF2α chain was assayed by incubating polyI:polyC or 3'-UTR transcript with the ribosome fraction from rabbit reticulocyte lysate in the presence of [γ-$^{32}$P]ATP for 20 min at 30° C. as described [49] and subjecting the reaction mixture to electrophoresis in 10% polyacryamide gels containing sodium dodecyl sulfate.

Nuclease Sensitivity Mapping

RNA (60 pmol), dephosphorylated with calf alkaline phosphatase and 5' end-labeled with [γ-$^{32}$P]ATP and T4 polynucleotide kinase, was purified on a 6% polyacrylamide gel in 8 M urea before its digestion for 20 min at 30° C. with 1 unit of RNase T1 (Worthington) or RNase U2, or 0.15 unit of V1 nuclease (Pharmacia). The mixture was made 9 M in urea, cooled on liquid nitrogen and separated on an 8% polyacrylamide sequencing gel.

Example 1

2-AP Inhibits Splicing of TNF-α Precursor Transcripts in Transfected Cells

BHK-21 cells were transfected with an intact human TNF-α gene (pTNF-α; FIG. 1C). Transient expression of TNF-α RNA transcripts was monitored by RNase protection analysis using probes complementary to adjacent portions of TNF-α5' flank and exon 1, in which 169 nt are protected by correctly initiated RNA, or of TNF-α3'-UTR and downstream sequences, in which 83 nt are protected by RNA with a correct 3' end (FIG. 2A). Endogenous hamster TNF-α mRNA was not detected by these probes. Expression of TNF-α RNA transcripts was sensitive to 2-AP in the culture medium, which led to a reduction at 2 mM and full inhibition at 6 mM. RNA transcripts with authentic 5' or 3' ends were expressed concomitantly and inhibited to the same extent by 2-AP. Hence, premature termination of transcription, which could affect processing of precursor RNA [50], is not the basis for the observed inhibition.

2-AP inhibits splicing of TNF-α precursor transcripts induced in human peripheral blood mononuclear cells [13]. In FIG. 2B, transient expression of TNF-α precursor transcripts (700-nt band) and spliced mRNA (341-nt band) was quantitated in pTNF-α-transfected cells, using an antisense RNA probe covering part of intron 2, exon 3, intron 3 and part of exon 4. Precursor transcripts were abundant at 20 h after transfection and then declined to low levels. Splicing of these transcripts resulted in the accumulation of mRNA, maximal by 24 h. Addition of 2-AP had a pronounced effect on this pattern of expression, leading to enhanced accumulation of precursor transcripts and to their sustained expression (FIGS. 2B and C). By contrast, expression of spliced TNF-α mRNA was strongly inhibited (FIGS. 2B and D). Expression of a cotransfected CAT gene was not affected by 2-AP. The opposite responses of precursor transcripts and mRNA to 2-AP show that it inhibits splicing of TNF-α mRNA encoded by a transfected human gene [13]. Sequences within this gene thus confer sensitivity to 2-AP.

Example 2

3'-UTR Sequences Are Required for Inhibition of TNF-α mRNA Splicing by 2-AP

To examine whether TNF-α gene promoter or 5'-UTR sequences respond to 2-AP, cells were transfected with p5'CAT, in which 821 bp from the TNF-α gene, comprising 652 bp preceding the transcription start site, the 5'-UTR and the first 6 codons of the open reading frame are abutted to the CAT gene (p5'CAT, FIG. 1A). Expression of CAT mRNA proceeded unabated at 10 mM 2-AP (FIG. 2E), a concentration that inhibited expression of TNF-α mRNA from pTNF-α (FIG. 2B). Sequences mediating the response to 2-AP thus map downstream from the TNF-α 5'-UTR.

Figure 2F:
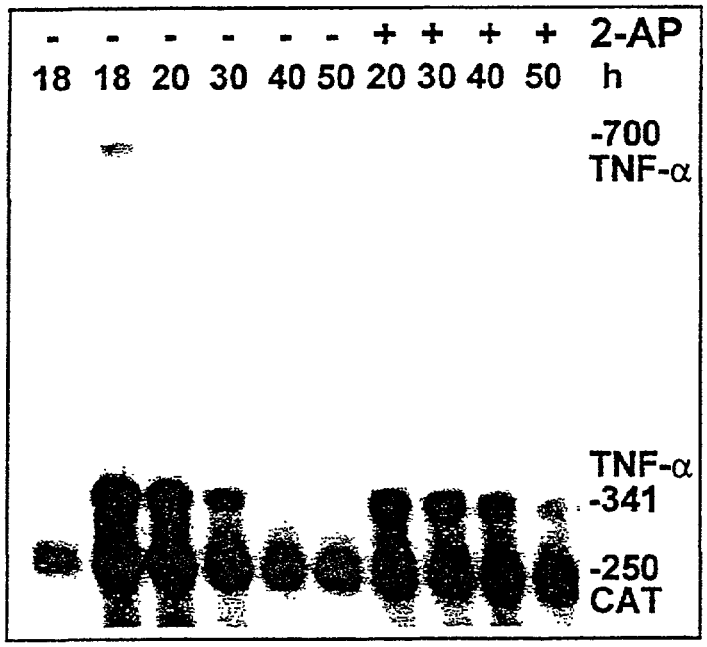

In FIG. 2F, BHK-21 cells were transfected with pTNF-α(Δ3'UTR) which lacks 573 terminal bp of the 792-bp 3'-UTR and the 3'-end processing signal (FIG. 1D). Expression of precursor transcripts and mRNA was abundant and as transient as for the complete gene (FIG. 2B), yet expression of mRNA was no longer inhibited by 2-AP, nor was there any enhanced accumulation of precursor transcripts (FIG. 2F). Although removal of most of the TNF-α3'-UTR led to loss of 2-APRE-mediated regulation of splicing by 2-AP, the expressed precursor transcripts showed normal kinetics of splicing. Hence, the deleted 3'-UTR sequences are not required for splicing but solely for the regulation of this process.

Expression of CAT mRNA carrying the portion of the TNF-α3'-UTR that is absent in pTNF-α(Δ3'UTR), in cells transfected with p5'CAT(3'UTR-α) FIG. 1B), was unaffected by 2-AP, showing that when linked to this intronless gene, the TNF-α3'-UTR sequences do not mediate an inhibition of mRNA expression nor its destabilization by 2-AP.

Example 3

2-AP Does Not Inhibit TNF-β Gene Expression at Splicing

In lymphoid cells, increasing doses of 2-AP led to a coordinate decline in TNF-β precursor transcripts and spliced mRNA, supporting an inhibition at transcription rather than at splicing [13]. The entire human TNF-β gene (pTNF-β, FIG. 1E) was transfected and expression of TNF-β RNA was monitored with an antisense RNA probe covering adjacent segments of intron 3 and exon 4 (FIG. 3A). Unspliced precursor transcripts (637-nt protected fragment) were expressed transiently in large amounts while expression of TNF-β mRNA (571 nt) was to lower levels. This ratio attests to slow excision of intron 3 from human TNF-β precursor transcripts in BHK-21 cells. Addition of 2-AP did not elicit any increase in TNF-β precursor transcripts; instead, precursors and mRNA both declined.

The antisense RNA probe used in FIG. 3B overlaps TNF-β exons 1–3 and part of intron 3. Precursor transcripts protect 169 nt while partially spliced precursor transcripts protect fragments of 324 and 275 nt. A 214-nt fragment became prominent by 24 h. This fragment is protected by spliced RNA molecules in which exons 2, 3 and 4 are joined. Fully spliced mRNA (which protects a 263-nt fragment), though seen in lymphoid cells [13], was not detected in BHK-21 cells (FIG. 3B). Transfection of pTNF-β yielded transient expression of precursor transcripts whose decline was accompanied by the appearance of spliced RNA (214-nt band). Again, formation of spliced TNF-β RNA was relatively slow and the yield was low. Addition of 2-AP led to a decrease in spliced RNA (lanes 3 vs. 6) as well as precursor transcripts (lanes 2 vs. 5). This response, seen in FIGS. 3A and B, stands in marked contrast to that of the TNF-α gene (FIG. 2) and indicates that 2-AP fails to inhibit expression of a transfected TNF-β gene at mRNA splicing.

Example 4

2-AP Inhibits Splicing of TNF-β Precursor Transcripts Carrying TNF-3'-UTR Sequences In FIGS. 3C and D, transfection was with pTNF-β (3'UTR-α) (FIG. 1F), in which the TNF-β3'-UTR is truncated 160 bp downstream from the stop codon and joined to a 823-bp TNF-α gene fragment comprising 573 terminal bp of the 3'-UTR, the polyadenylation site and downstream sequences. Addition of 2-AP led to a shift from spliced RNA (214-nt band) to precursor transcripts which increased strongly (FIG. 3D, lanes 1–4 vs. 5–7). 2-AP failed to block transcription of the chimeric TNF-β(3'UTR-α) gene, inhibiting instead the excision of TNF-β introns 2 and 3 required for expression of spliced RNA. These findings are corroborated by use of TNF-β intron 3/exon 4 probe (FIG. 3C). Again, addition of 2-AP led to a strong increase in precursor transcripts and a concomitant decline in spliced RNA, resulting in a pronounced rise in their ratio (lanes 1–4 vs. 5–7). By contrast, in cells transfected with pTNF-β (Δ3'UTR) (FIG. 1G), lacking the TNF-α insert of pTNF-β (3'UTR-α), expression of spliced TNF-β RNA was insensitive to 2-AP.

Addition of CHX led, in the pTNF-β(3'UTR-α)-transfected cells, to enhanced expression of both precursor transcripts and spliced RNA (FIGS. 3C and 3D, lanes 2 vs. 8). Expression of spliced RNA was shifted to earlier times, followed by a decline in precursor transcripts and, more slowly, in spliced RNA (lanes 8–9). Here, too, generation of spliced RNA was inhibited by 2-AP (lanes 8 vs. 10) while precursor transcripts increased (lanes 9 vs. 11), the ratio of precursor transcripts to spliced mRNA increasing strongly. Thus, when their expression is enhanced by CHX, splicing of TNF-β precursor transcripts carrying a TNF-α3'-UTR is also susceptible to inhibition by 2-AP.

Expression of TNF-β mRNA from both pTNF-β and pTNF-β(3'UTR-α) is sensitive to 2-AP. However, the response to 2-AP is shifted from an apparent inhibition of transcription for pTNF-β to inhibition of splicing for pTNF-β(3'UTR-α). Replacement of part of the TNF-β3'-UTR with TNF-α3'-UTR sequences renders splicing sensitive to 2-AP at multiple sites, shown in FIGS. 3C and 3D for joining of TNF-β exons 2, 3 and 4. The observation that 2-AP fails to inhibit expression of mRNA from p5'CAT(3'UTR-α), yet inhibits mRNA expression from pTNF-β(3'UTR-α) at splicing, emphasizes a requirement for exon/intron junctions in addition to TNF-α3'-UTR sequences. However, there is no requirement for TNF-α exons or introns per se, since pTNF-β(3'UTR-α) contains only TNF-β exon/intron junctions, demonstrating a transcript-independent function of the 2-APRE element. A cis-acting element that renders splicing sensitive to inhibition by 2-AP thus is located within the TNF-α3'-UTR.

Example 4A

Figure 3E:
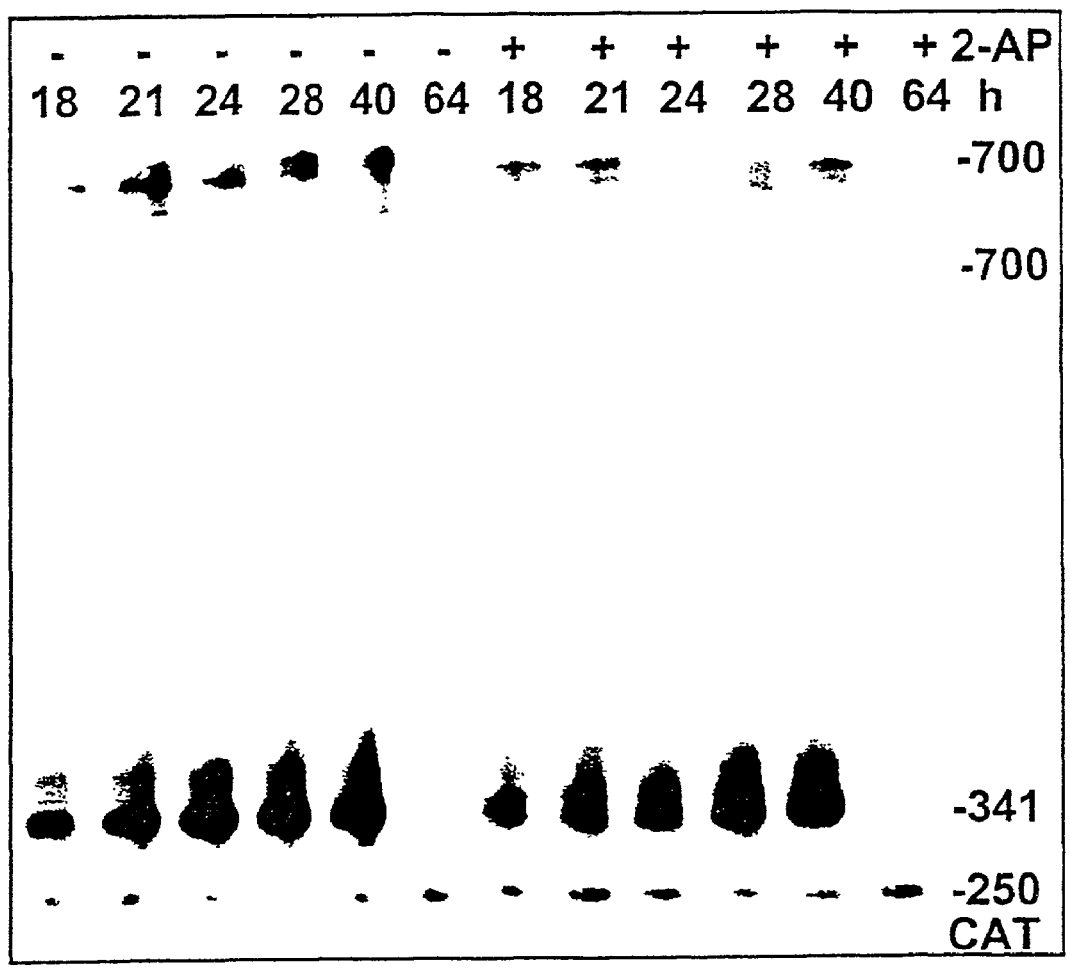

Splicing of TNF-α Precursor Transcripts Carrying TNF-β3'-UTR Sequences is Insensitive to 2-AP As seen from the responses of constructs pTNF-α, pTNF-α(Δ3'UTR), pTNF-β, and pTNF-β(3'UTR-α) (FIG. 1C-F), the TNF-α3'-UTR confers sensitivity to 2-AP at splicing of precursor transcripts while the TNF-β3'-UTR lacks this property. This leads one to predict that splicing of precursor transcripts encoded by the reciprocal chimeric gene, pTNF-α(3'UTR-β) (FIG. 1H), should proceed unabated in the presence of 2-AP. In pTNF-α(3'UTR-β), the TNF-α gene was truncated 219 bp into the 3'-UTR and joined to a 572-bp TNF-β gene fragment comprising the 3'-terminal 389-bp of the 628-bp 3'-UTR, the polyadenylation site and downstream sequences. Expression of spliced mRNA (341-nt band) from pTNF-α(3'UTR-β) failed to decline when 2-AP was present, nor did precursor transcripts (700 nt) increase (FIG. 3E). Splicing of TNF-α mRNA carrying TNF-β3'-UTR sequences thus is insensitive to inhibition by 2-AP, again showing that a 2-AP response element (2-APRE) resides specifically in the TNF-α3'-UTR.

Example 5

Activation of PKR by RNA Deriving from the TNF-α3'-UTR

Figure 4B:
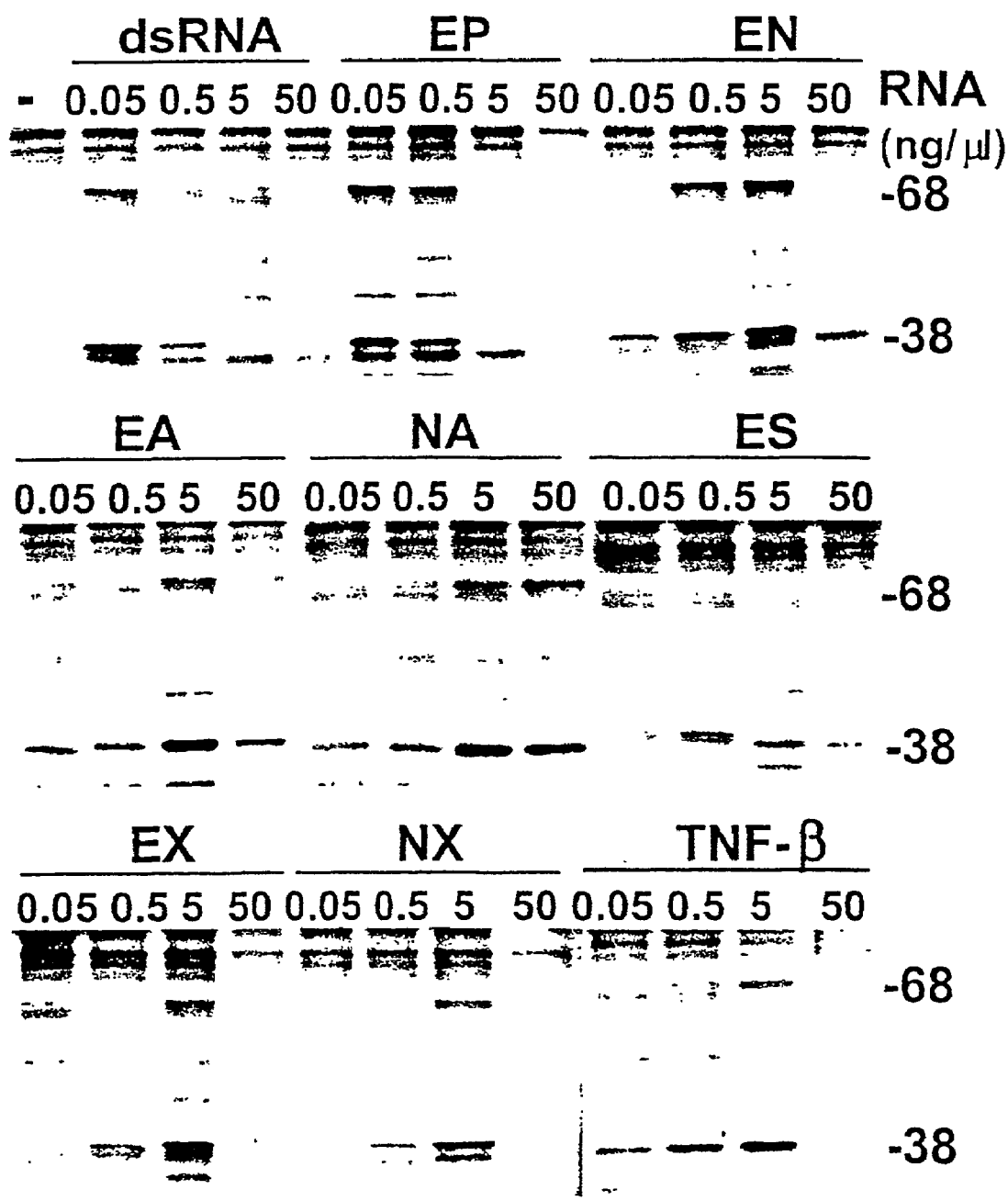
Figure 4C:
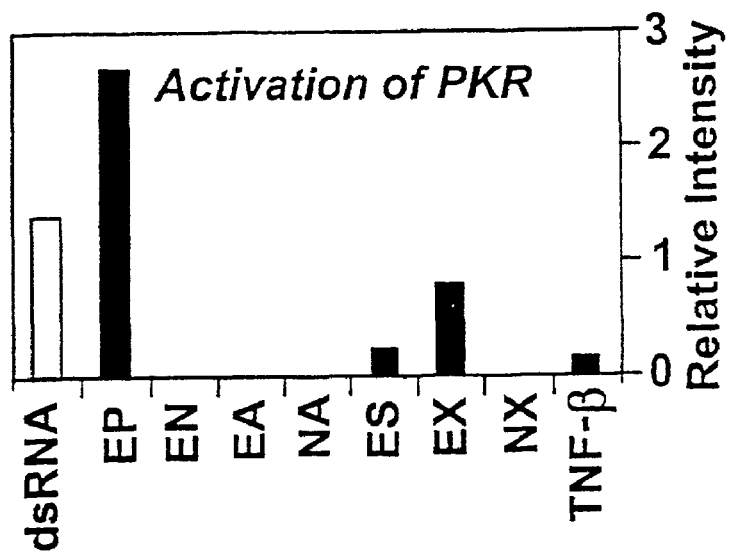

T7 RNA transcripts were generated from various fragments of TNF-α3'-UTR DNA (FIG. 4A) and from TNF-β3'-UTR DNA. To eliminate any contaminating dsRNA, these transcripts were purified by gel electrophoresis arid CF-11 cellulose chromatography [38]. At low RNA concentration (0.05 ng/ml), RNA derived from the 104-bp Eco RI-PstI fragment (3'UTR-αEP) activated PKR even more strongly than dsRNA, as judged by phosphorylation of the PKR (68 kDa) and eIF2α (38 kDa) bands in the ribosome fraction of rabbit reticulocyte lysate (FIG. 4B). Like dsRNA, 3'UTR-α EP RNA induced phosphorylation of PKR and eIF2α at low but not high RNA concentrations. RNAs derived from longer or other fragments of the TNF-α3'-UTR, or from the TNF-β3'-UTR, also induced phosphorylation of the 68 kDa band, but only at significantly higher RNA concentrations: 0.5 ng/ml for EN and 5 ng/ml for the other RNA species (FIG. 4B). As inducer of PKR phosphorylation, which is a primary indicator of activation of PKR, 3'UTR-αEP RNA stood out with the highest molar specific activity (FIG. 4C). Thus, the EP domain in the TNF-α3'-UTR, located well upstream of the AU-rich element (FIG. 4A), encodes an RNA that at low concentrations, strongly activates PKR in vitro.

Example 6

2-AP Inhibits Activation of PKR by 3'UTR-αEP RNA

Figure 4D:

Phosphorylation of PKR and eIF2α, driven by the purified 3'UTR-αEP RNA T7 transcript, was inhibited progressively by 1 and 5 mM of 2-AP (FIG. 4D). Activation of PKR by 3'UTR-αEP RNA was less sensitive to 1 mM 2-AP than that by dsRNA, again attesting to the potent PKR-activating activity of the former. These results show that 3'-αEP RNA activates PKR in a 2-AP-sensitive manner.

Example 7

Structure of 3'UTR-αEP RNA

The structure of 3'UTR-αEP RNA transcript was analyzed by T1, U2 and V1 RNase sensitivity mapping (FIG. 5). 3'UTR-αEP RNA forms a stable, 5'-proximal 48-nt stem-loop containing 17 base pairs (DG=−59 kJ at 30° C.). As calculated by the RNADraw and mfold algorithms, this stem-loop structure persists in the longer EP-containing RNA fragments shown in FIG. 4A.

Analysis of a 104-nt RNA transcribed from the human TNF-α2-APRE by nuclease sensitivity mapping thus reveals a stable stem-loop structure containing 17 bp, including 10 G:C pairs. The DNA encoding this stem loop is denoted herein by SEQ ID NO:2 (Table 1). This structure is conserved in human, porcine, rabbit, bovine and goat TNF-α genes (FIG. 5). Phylogenetic conservation is most pronounced in the upper stem and 6-nt loop which thus are likely to be involved in the activation of PKR. This folding is preserved in longer human TNF-α3'-UTR RNA fragments containing the 2-APRE. Moreover, the location of the 2-APRE within the human TNF-α3'-UTR, halfway between the stop codon and the AU-rich motif and about 200 nt upstream of the latter, is conserved in the porcine, rabbit, and bovine genes.

By contrast, no significant sequence homology of the 2-APRE is found with adenovirus VA RNA which binds to and inhibits PKR [34], nor with HIV-1 TAR [51], human a-tropomyosin 3'-UTR [33] or reovirus S1 3'-UTR [32] which were reported to activate PKR in vitro. Although 2-AP may affect splicing of murine c-fos mRNA [52], this RNA lacks a 2-APRE-like sequence. No similar structure, moreover, is found in the human TNF-β3'-UTR.

Example 8

The 3'UTR-αEP Domain is the 2-APRE of the TNF-α Gene

To test the concept that the EP domain in the TNF-α3'-UTR, capable of activating PKR in vitro (FIG. 4), mediates the sensitivity of TNF-α mRNA splicing to 2-AP (FIG. 2B), it was abutted to the TNF-α(Δ3'UTR) and TNF-b genes, neither of which show any sensitivity to 2-AP at mRNA splicing (FIGS. 2 and 3). In the constructs thus generated (pTNF-α(3'UTR-αEP), FIG. 1I and pTNF-β(3'UTR-αEP), FIG. 1J), the EP domain is followed by polyadenylation signal sequences of the TNF-β gene.

Figure 6A:
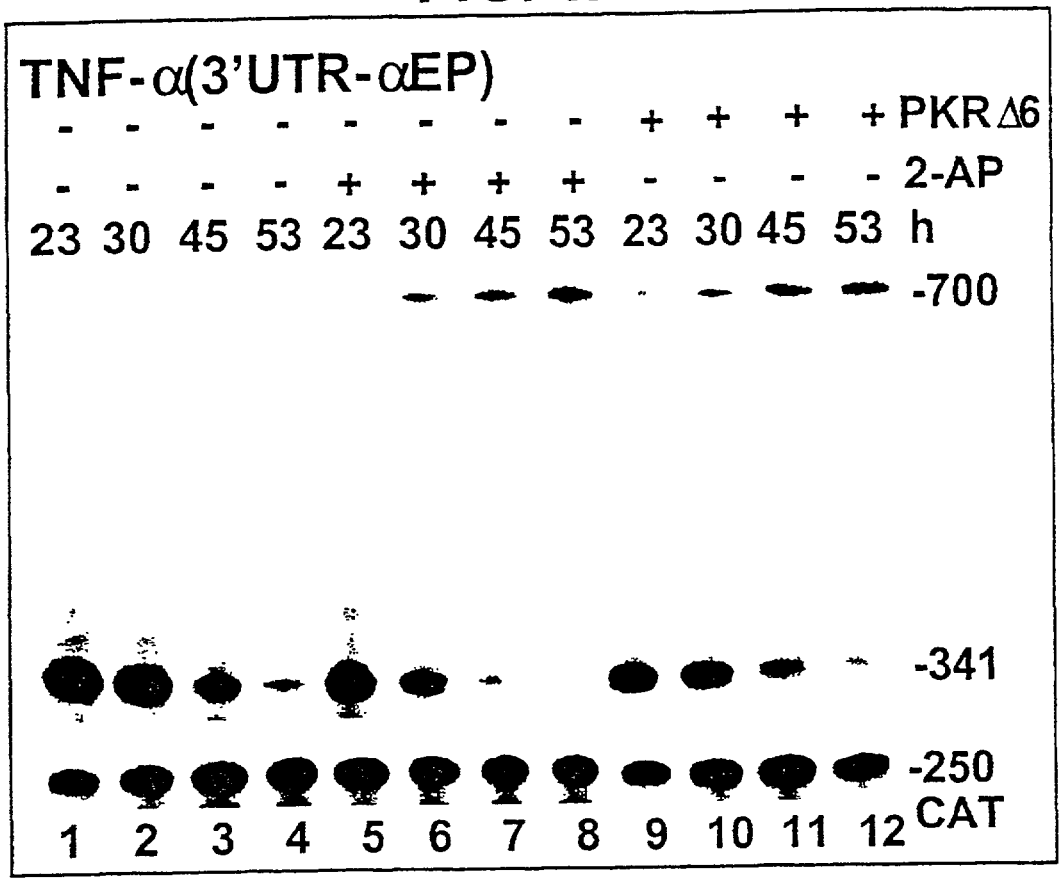
Figure 6B:
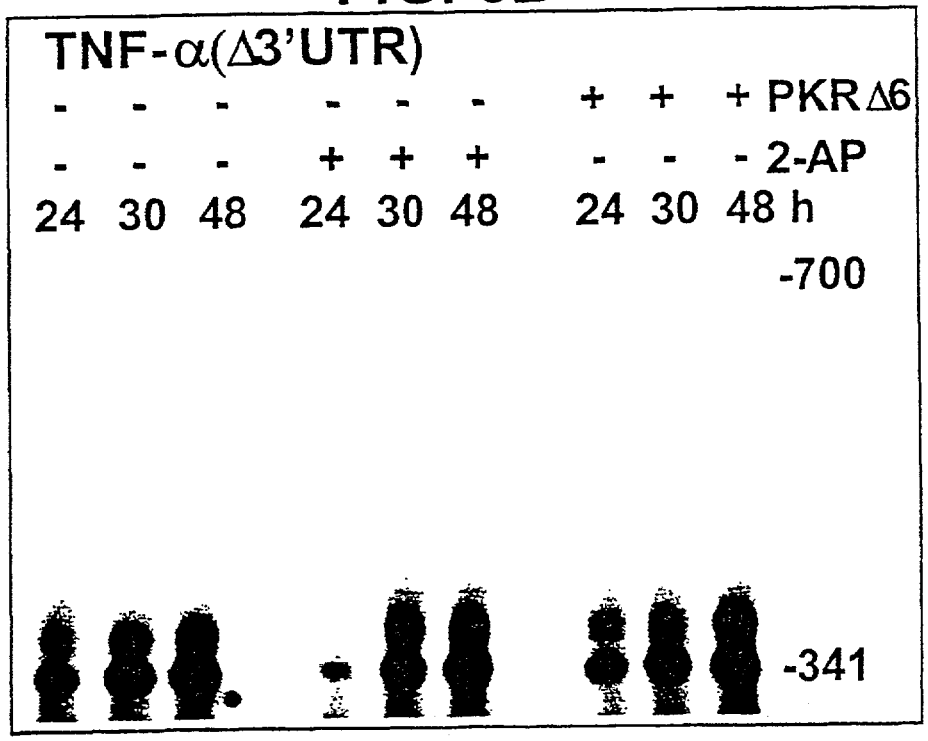

BHK-21 cells transfected with pTNF-α(3'UTR-αEP) showed transient expression of precursor transcripts and spliced mRNA (FIG. 6A, lanes 1–4). Addition of 2-AP at 20 h elicited a progressive rise in precursor transcripts (up to 36-fold at 53 h), coupled with a decline in mRNA (lanes 5–8). Likewise, in cells transfected with pTNF-β(3'UTR-α EP), addition of 2-AP led to a pronounced shift from spliced mRNA to precursor transcripts (FIG. 7A). Thus, introduction of the 3'UTR-αEP fragment suffices for a gain of function, rendering splicing of precursor transcripts sensitive to inhibition by 2-AP, whether these arise from the TNF-α or TNF-β gene, demonstrating a transcript-independent function of the 2-APRE element. Hence, the 3'UTR-αEP domain is a functional 2-APRE.

Example 9

The Function of the 2-APRE in mRNA Splicing Involves Activation of PKR

On one hand, RNA transcribed from the 3'UTR-αEP domain is able to activate PKR; on the other hand, this domain renders mRNA splicing sensitive to inhibition by the PKR inhibitor, 2-AP. These results raised the possibility that PKR functions as a trans-acting factor that regulates mRNA splicing in precursor transcripts that carry the 2-APRE. To obtain direct evidence for this concept, cells were co-transfected with TNF gene constructs and a vector expressing PKRΔ6, a transdominant-negative mutant of PKR that prevents the activation of wild type PKR [20]. If PKRΔ6 were to block the activation of endogenous PKR, it should cause inhibition of mRNA splicing in a manner resembling 2-AP. Indeed, as seen in FIG. 6A for pTNF-α(3'UTR-αEP) and in FIG. 7B for pTNF-β(3'UTR-αEP), the effect of PKRΔ6 cotransfection was strikingly similar to that of addition of 2-AP, shifting the pattern of RNA molecules from spliced to unspliced forms. In FIG. 6A, the effect was particularly pronounced at later times when PKRΔ6 expression should become more prominent (lanes 1–4 vs. 9–12) but even at the early times a reduction in spliced RNA was evident. This shift to unspliced RNA forms was not observed for the TNF-α(Δ3'UTR) gene (FIG. 6B) nor for the TNF-β gene (FIG. 7C) and thus requires the 2-APRE. For the TNF-β gene, total expression of RNA was reduced by PKRΔ6, reflecting the earlier results with 2-AP (FIGS. 3A and B).

Conversely, FIG. 8 shows that overexpression of wild-type PKR enhances splicing in a 2-APRE-dependent manner. Co-transfection with pPKR, a vector expressing wild-type PKR, led to a shift from unspliced RNA into mRNA encoded by pTNF-α(3'UTR-αEP), the ratio of mRNA over precursor transcripts increasing up to 20-fold by 45 h. Such enhancement was absent when pTNF-α(Δ3'UTR) was used instead.

When PKR was co-transfected, moreover, the amount of mRNA expressed by pTNF-α(3'UTR-αEP) was significantly greater than that expressed by pTNF-α(Δ3'UTR), despite higher levels of unspliced precursor transcripts in cells transfected by the latter construct (FIG. 8). This result shows that the ability to respond to PKR at the splicing step enables a more efficient production of TNF-α mRNA.

The 2-APRE renders mRNA splicing dependent on activation of PKR, which can be abrogated by 2-AP or expression of PKRΔ6 and enhanced by expression of wild-type PKR. Our results show that activation of PKR is not only required for splicing of mRNA when precursor transcripts contain the 2-APRE but also makes it far more efficient.

These results show that activation of PKR is essential for splicing of mRNA when precursor transcripts contain the 2-APRE but not when they lack it. The 2-APRE thus renders mRNA splicing dependent on the activation of PKR, which can be abrogated by 2-AP or by PKRΔ6 (FIG. 1).

Accordingly, the 2-APRE represents a novel cis-acting element that controls splicing. In the presence of 2-AP, the decline in 2-APRE-containing mRNA was accompanied by a strong increase in precursor transcripts (FIGS. 2C and 2D; [13]) This pronounced shift from mRNA to pre-mRNA is consistent with an inhibition at splicing rather than enhanced decay of mRNA. Located about 200 nt upstream of the AU-rich motif, the 2-APRE is in a region not involved in destabilization of TNF-α mRNA. The possibility that the 2-APRE would render precursor transcripts more stable in the presence of 2-AP, yet mRNA less stable, is not supported by RNA chase experiments. In lymphoid cells, 2-AP does not reduce stability of TNF-α mRNA nor does it cause a perceptible stabilization of TNF-α precursor transcripts [13]. Deletion of 3'-UTR sequences, including the 2-APRE as well as the AU-rich motif, did not render the mRNA noticeably more stable (FIGS. 2B vs. 2F).

Thus, a novel role for the 3'-UTR, in the control of mRNA splicing has been shown. A regulatory sequence, 2-APRE, within the human TNF-α3'-UTR is a cis-acting element that renders splicing of precursor transcripts dependent upon the activation of the RNA-activated eIF2α kinase PKR. That the 2-APRE is a cis-acting element is shown by the finding that addition of the kinase inhibitor 2-AP, or co-transfection with a transdominant-negative mutant of PKR (PKRΔ6), leads to a severe inhibition of splicing of TNF-α mRNA but not of TNF-β mRNA. Deletion of the 2-APRE, moreover, or its replacement by TNF-β3'-UTR sequences, frees splicing of TNF-α precursor transcripts from a dependency on PKR activation, while insertion of the 2-APRE into the TNF-β3'-UTR leads to gain of this control (FIG. 1).

Both genetic (PKRΔ6) and biochemical evidence (2-AP) support the conclusion that activation of PKR is required for splicing, provided the 2-APRE is present in the precursor transcript. Thus, PKR responds as trans-acting factor to the 2-APRE. It has thus been shown that RNA encoded by the 2-APRE strongly activates PKR in vitro and induces eIF2α phosphorylation, supporting this functional link.

Activation of PKR is, however, not only necessary for splicing of mRNA when precursor transcripts contain the 2-APRE but also makes it more efficient. Overexpression of PKR leads to greatly facilitated splicing of TNF-α precursor transcripts, provided they contain the 2-APRE.

The results show a novel function for the RNA-activated eIF2α kinase, PKR, in the regulation of splicing. Precursor transcripts containing the 2-APRE are not spliced when the function of PKR is inhibited by 2-AP, which blocks the ATP-binding site in the protein [30], or by expression of a transdominant-negative mutant PKR which blocks trans-autophosphorylation of the enzyme, obligatory for its activation [20]. Hence, splicing of human TNF-α precursor transcripts is dependent on the activation of PKR. Cells expressing the TNF-α gene contain constitutive, low levels of PKR that suffice to fulfill this requirement for splicing since the phenotype of the 2-APRE is manifested only in conditions where activation of PKR is inhibited. Upon removal of the 2-APRE, the dependency of the splicing process on PKR activation is lost.

The finding that PKR is a trans-acting factor required for splicing of TNF-α but not TNF-β precursor transcripts reveals a selective mode of action for this protein kinase, apparently elicited through local activation by a highly ordered structure within the 2-APRE. Activation of PKR requires its dimerization on RNA [22, 23] which therefore must be induced by the 2-APRE.

Located within precursor transcripts expressed in the cell, the 2-APRE is able to render splicing dependent on the activation of PKR in a manner that can be inhibited by 2-AP or PKRΔ6. The 2-APRE in the human TNF-α gene thus represents a specific structure within the 3'-UTR of a cellular mRNA that is able to activate PKR in a manner that permits not only the phosphorylation of eIF2α chains but also the splicing of an mRNA.

Activation and inhibition of PKR by RNA are dependent on the length and position of double-helical regions having the A conformation, rather than on their specific sequence. Noncontiguous short helices of RNA can cooperate in binding of PKR and thereby, in its activation [39], properties that characterize the 2-APRE as well. Although the 2-APRE duplex is discontinuous, it complies with conformational constraints typical of highly structured RNAs. Remarkably, EP RNA is an even more potent activator of PKR than dsRNA, and unlike human delta hepatitis agent RNA [31], it also induces eIF2α phosphorylation (FIG. 5). Consistent with this property, when supported by the 2-APRE, activation of PKR and phosphorylation of eIF2α are less sensitive to inhibition by 2-AP than when mediated by dsRNA. Splicing of TNF-β precursor transcripts carrying an inverted TNF-α3'-UTR sequence is as sensitive to inhibition by 2-AP as splicing of TNF-β(3'UTR-α) transcripts, supporting the concept that structure rather than sequence of the 2-APRE is important for its function in splicing control.

The involvement of PKR in splicing and the role of the 2-APRE therein are clearly distinct from mechanisms that affect specific splice sites, e.g., in alternative mRNA splicing. Constitutive and alternative pre-mRNA splicing is controlled by reversible protein phosphorylation in which the activity of kinases and phosphatases is coordinated [42]. SR protein kinases and clk/Sty [52, 53] phosphorylate splicing factors that contain an RS domain. SR protein kinases, however, regulate splicing generally rather than selectively as shown here for the human TNF-α gene. The broad range of activity of the SR kinases differs from the more restricted PKR-dependent splicing control described here. The fact that splicing of IL-1β precursor transcripts [13], as well as TNF-α precursor transcripts lacking the 2-APRE, is insensitive to 2-AP, indicates that 2-AP does not inhibit SR protein kinases or RNA helicases required for constitutive splicing.

Accordingly, the 2-APRE represents the first example of a novel class of highly ordered cis-acting RNA elements involved in mRNA splicing control.

Example 10

Self-elimination of Splicing Control Element 2-APRE

The exonic 2-APRE from the TNF-α gene is a cis-acting, portable element that confers splicing control. Upon transport into the cytoplasm, however, localized activation of PKR by the 2-APRE residing in resulting mature mRNA is expected to reduce the translation efficiency of the resulting mRNA, through local activation of PKR and phosphorylation of the eIF2α subunit in the cytoplasm. The advantage gained from control of splicing by the 2-APRE may thus be offset by a loss in translation efficiency. A solution to this problem, for applications in biotechnology and gene therapy, is provided as illustrative example by construct pTNF-α (Δ3'UTR-i3EP) (FIG. 1K). In pTNF-α(Δ3'UTR-i3EP), the 2-APRE was moved away from its exonic location within the TNF-α3'-UTR into intron 3 of the TNF-α gene.

After first rendering mRNA splicing in cis dependent upon the activation of RNA-activated eIF2α kinase, the intronic 2-APRE is spliced out of the mRNA together with the remainder of the intron, yielding a 2-APRE-free mRNA that will undergo more active translation because it cannot support 2-APRE-mediated activation of the kinase in the cytoplasm.

Using an intronic 2-APRE, its effect will be restricted to the nucleus, where it will locally activate PKR to promote mRNA splicing. Using nuclear localization sequence [55]-PKR fusion constructs, futhermore, nuclear localization of PKR may be achieved. In this way, regulation of splicing may be uncoupled from translational control.

Example 11

Use of Splicing Control Element 2-APRE in Combination with Regulated Expression and/or Activity of the RNA-activated eIF-2α kinase Insertion of a cis-acting element, exemplified by the 2-APRE, into a desired gene renders splicing of mRNA encoded by this gene dependent on the activity of a kinase exemplified by PKR. Methods known in the art can now be used to obtain a regulated expression system based on 2-APRE-mediated regulation of splicing by introducing low molecular weight compounds in the medium of a cell culture or in a transgenic organism. For this purpose, the target element in the expression vector (e.g., the 2-APRE) is combined with a regulated effector provided by manipulating the expression and/or activity of eIF2α kinase (e.g., PKR). Such a system may be combined with already existing vectors in which expression is regulated at the level of transcription or translation.

The 2-APRE may be integrated at different positions, whether intronic as exemplified by pTNF-α(Δ3'UTR-i3EP) or exonic as exemplified by pTNF-α(3'UTR-αEP) or pTNF-β(3'UTR-αEP); in an exonic location, the 2-APRE may be placed 3' or 5' to the open reading frame of the desired protein, in order to allow optimal function in splicing regulation while minimizing possible side effects on transcription yield, mRNA half-life, and translation yield. Such placement may be optimized using reporter genes, e.g., firefly luciferase [56] and green fluorescent protein mutants [57]. The promoter of this vector construct will be constitutive with respect to manipulation of cells and the application of regulating compounds to be described below.

Examples of cells useful for application of the invention are BHK and CHO cells. Regulated expression of the desired gene or of the reporter gene can be analyzed at the protein as well as at the RNA level.

A trans-acting regulator implicated for the 2-APRE is PKR. Downregulation of PKR should reduce splicing, while overexpression of PKR should increase it. Although overexpression of PKR occurs, for example, in interferon-treated cells, the enzyme remains inactive as long as viral dsRNA is lacking, thus allowing translation to proceed unabated and cells to grow normally [67]. Methods are known in the art to make either expression of PKR or activity of PKR regulatable by external means.

For example, expression can be controlled by use of the TET-off system [7]. Transactivator-containing cells are supertransfected with the PKR gene under control of the tetracycline-dependent promoter. Thus, in the presence of tetracycline the promoter should be off and in its absence, overproduction of PKR (or of a trans-dominant-negative mutant of PKR) should take place.

Activity of PKR can be modulated, for example, by use of fusion proteins between PKR and a steroid hormone receptor element. In many examples, it was shown that such fusion proteins are fully dependent on the respective hormone, e.g., progesterone, estradiol, or tamoxifen [58, 59, 60]. Either wild type PKR and a negative dominant mutant PKR can be used. The function of these fusion proteins in dependence on the steroid hormone is tested by examining autophosphorylation of the PKR fission protein or its targets, endogenous PKR or the eIF-2α chain. Furthermore, such regulation can be tested with respect to expression of a reporter gene in a co-transfected splicing vector as described above.

Another way to manipulate PKR activity is exemplified by 2-AP or other adenine analogs [61], or by calcium ions [65].

To achieve an even wider range of splicing regulation through the cis-acting element (e.g., 2-APRE), one may inhibit the endogenous PKR activity of cell by stably integrating, for example, a transdominant negative mutant of PKR, or a PKR-inhibitory protein exemplified by vaccinia virus E3L [62] or K3L genes [63], or an RNA that inhibits the activation of PKR exemplified by adenovirus VA RNA [34] and by Epstein-Barr virus Eber RNA [66] and expressing such a PKR-inhibitory gene to low levels by use, for example, of the TET-off system. In cell clones in which this has been achieved, a regulatable PKR expression vector can then be introduced, to allow control of the level of functional PKR activity over a wide range.

REFERENCES

1. Wilmut, I, Whitelaw, CBA (1996) Reprod Fertil Dev 6:625.
2. Clark A J, Cowper A, Wallace R, Wright G, Simons K P (199) Bio/Tech 7:487.
3. Webster J, Donofrio G, Wallace R, Clark A J, Whitelaw C B A (1997) Gene 192:239.
4. Whitelaw C B A, Archibald A L, Harris S, McClenaghan M, Simons J P, Clark A J (1991) Transg Res 1:3.
5. Kaufmann R J (1990) Techniques 2:221.
6. Simonsen C C, McGrogan M (1994) Biologicals 22:85.
7. Gossen M, Bujard H (1992) Proc Natl Acad Sci USA 89:5547.
8. Figge J, Wright C, Collins, C J, Roberts T M, Livingston D M (1988) Cell 52:713.

9. Karin M, Haslinger A, Holtgreve H, Cathala G, Slater E, Baxter J D (1984) Cell 36:371.
10. Ko M S H, Takahashi N, Sugiyama N, Takano T (1989) Gene 84:.
11. Wurm F M, Gwinn K A, Kingston, R E (1986) Proc Natl Acad Sci USA 83:5414.
12. Jarrous N, Kaempfer R (1994) J Biol Chem. 269:23141.
13. Jarrous N, Osman F, Kaempfer R (1996) Mol Cell Biol 16:2814.
14. Farrell, P J, Balkow, K, Hunt, T, Jackson, R J and Trachsel, H (1977) Cell 11:187–200.
15. Thomis, D C, and Samuel, C E (1993) J Virol 67:695–700.
16. Tanaka H, Samuel C E (1994) Proc Natl Acad Sci USA 91:7995.
17. Samuel C E (1993) J Biol Chem 268:7603.
18. Hershey J W (1991) Annu Rev Biochem 60:717.
19. Donze O, Jagus R, Koromilas A E, Hershey J W, Sonenberg N (1995) EMBO J 14:3828.
20. Koromilas A E, Roy S, Barber G N, Katze M G, Sonenberg N (1992) Science 257:1685.
21. Meurs E F, Galabru J, Barber G N, Katze M G, Hovanessian A G (1993) Proc Natl Acad Sci USA 90:232.
22. Bevilacqua, P C, and Cech, T (1996) Biochemistry 35:9983–9994.
23. Wu, S and Kaufman, R J (1997) J Biol Chem 272:1291–1296.
24. Buchman A R, Berg P (1988) Mol Cell Biol 8:4395.
25. Petitclerc D, Attal J, Theron M C, et al (1995) J Biotech 40:169.
26. Robertson, H D and Mathews, M B (1996) Biochimie 78:909–914.
27. Gerez L, Arad G, Efrat S, Ketzinel M, Kaempfer R (1995) J Biol Chem 270:19569.
28. Umlauf, S W, Beverly, B, Lantz, O and Schartz, R H (1995) Mol Cell Biol 15:3197–3205.
29. Neel, H, Gondran, P, Weil, D and Dautry, F (1995) Curr Biol 5:413–422.
30. Hu, Y and Conway, T W (1993) J Interferon Res 13:323–328.
31. Robertson, H D, Manche, L and Mathews, M B (1996) J Virol 70:5611–5617.
32. Henry, G L, McCormack, S J, Thomis, D C and Samuel C E (1994) J Biol Regul Homeost Agents 8:15–24.
33. Davis, S and Watson J C (1996) Proc Natl Acad Sci USA 93:508–513.
34. Clarke, P A, and Mathews, M B (1995) RNA 1:7–20.
35. Chu, W M, Ballard, R, Carpick, B W, Williams, B R and Schmid, C W (1998) Mol Cell Biol 18:58–68.
36. St-Johnston, D, Brown, N H, Gall, J G and Jantsch, M (1992) Proc Natl Acad Sci USA 91:7995–7999.
37. Schmedt, C, Green, S R, Manche, L, Taylor, D R, Ma, Y and Mathews, M B (1995) J Mol Biol 249:29–44.
38. Circle, D A, Neel, O D, Robertson, H D, Clarke, P A and Mathews, M B (1997) RNA 3:438–448.
39. Bevilacqua, P C, George, C X, Samuel, C E and Cech, T R (1998) Biochemistry 37:6303–6316.
40. Jeffrey, I W, Kadereit, S, Meurs, E F, Metzger, T, Bachmann, M, Schwemmle, M, Hovanessian, A G, and Clemens, M J (1995) Exp Cell Res 218:7–27.
41. Besse, S, Rebouillat D, Marie, I, Puvion Dutilleul, F, and Hovanessian, A G (1998) Exp Cell Res 239:379–392.
42. Misteli, T, Caceres, J F, Spector, D L (1997) Nature 387:523–527.
43. Kruys, V, Kemmer, K, Shakhov, A, Jongeneel, V, and Beutler, B (1992) Proc Natl Acad Sci USA 89:673–677.
44. Caput, D, Beutler, B, Hartog, K, Brown-Shimer, S, and Cerami, A (1986) Proc Natl Acad Sci USA 83:1670–1674.
45. Mijatovic, T, Kruys, V, Caput, D, Defrance, P, and Huez, G (1997) J Biol Chem 272:14394–14398.
46. Lewis, T, Gueydan, C, Huez, G, Toulme, J J, and Kruys, V (1998) J Biol Chem 273:13781–13786.
47. Gorman, C M, Mofat L F, and Howard, B H (1982) Mol Cell Biol 2:1044–1051.
48. Goldfeld, A E, Doyle, C, and Maniatis, T (1990) Proc Natl Acad Sci USA 87:9769–9773.
49. Rosen, H, Knoller, S, and Kaempfer, R (1981) Biochemistry 20:3011–3020
50. Biragyn, A, and Nedospasov, SA (1995) J Immunol 155:674–683.
51. Maitra, R K, McMillan, N A, Desai, S, McSwiggen, J, Hovanessian, A G, Sen, G, Williams, B R, and Silverman, R H (1994) Virology 204:823–827.
52. Zinn, K, Keller, A, Whittemore, L A, and Maniatis, T (1988) Science 240:210–213.
53. Gui, J F, Lane, W S, Fu, X D (1994) Nature 369:678–682.
54. Colwill, K, Pawson, T, Andrews, B, Prasad, J, Manley, J L, Bell, J C, and Duncan, P I (1996) EMBO J 15:265–267.
55. Autieri, M V, Agrawal, N (1998) J Biol Chem. 273:14731–14737.
56. Yin, D X, Zhu, L, Schimke, R T (1996) Anal Biochem. 235:195–201.
57. Chalfie, M, Tu, Y, Euskirchen, G, Ward, W W, Prasher, D C (1994) Science. 263: 802–805.
58. Banner, C D, Goos, Nilsson-A, Sjovall, J, Gustafsson, J A, Rafter, J J (1992) Anal Biochem. 200:163–170.
59. Chung, K C, Gomes, I, Wang, D, Lau, L F, Rosner, M R (1998) Mol Cell Biol. 18:2272–2281.
60. Kerkhoff, E, Rapp, U R (1997) Mol Cell Biol 17:2576–2586.
61. Legon, S, Brayley, A, Hunt, T, Jackson, R J (1974) Biochem Biophys Res Commun. 56:745–752.
62. Davies, M V, Chang, H W, Jacobs, B L, and Kaufman, R J (1993) J Virol. 67:1688–1692.
63. Davies, M V, Elroy-Stein, O, Jagus, R, Moss, B, and Kaufman, R J (1992) J Virol. 66:1943–1950.
64. Zuker, M. (1989). Science 244:48–52.
65. Srivastava, S P, Davies, M V, Kaufman, R J (1995) J Biol Chem. 270: 6619–16624.
66. Elia, A, Laing, K G, Schofield, A, Tilleray, V J, Clemens, M J (1996) Nucleic Acids Res. 24:4471–4478.
67. Der, S D, Lau, A S (1995) Proc Natl Acad Sci USA. 92:8841–8845.

The invention claimed is:

1. A cis-acting nucleotide sequence which is capable of rendering the removal of introns from a precursor transcript encoded by any gene, which gene harbors at least one such cis-acting nucleotide sequence, occurring during the production of mRNA of said gene, dependent upon activation of a trans-acting factor, said trans-acting factor being the RNA-activated protein kinase (PKR) which is capable of phosphorylating the α-subunit of eukaryotic initiation factor 2, and wherein said cis-acting nucleotide sequence is derived from the 3' untranslated region of the human tumor necrosis factor α gene (TNF-α-3'UTR) and consists of a sequence selected from the group consisting of SEQ ID NO:1 and SEQ ID NO:2.

2. The cis-acting nucleotide sequence according to claim 1 wherein said cis-acting nucleotide sequence is derived from the 3' untranslated region of the human tumor necrosis factor α gene (TNF-α-3'UTR) and consists of the nucleotide sequence denoted by SEQ ID NO:1.

3. The cis-acting nucleotide sequence according to claim 1 wherein said cis-acting nucleotide sequence is derived from the 3' untranslated region of the human tumor necrosis factor α gene (TNF-α-3'UTR) and consists of the nucleotide sequence as denoted by SEQ ID NO:2.

4. The cis-acting nucleotide sequence according to claim 3 wherein said gene encodes a protein selected from the group consisting of enzymes, hormones, growth factors, cytokines, structural proteins, industrially applicable proteins, agriculturally applicable proteins, a protein which is a therapeutic product, a protein which is an agricultural product, and a protein which is an industrially applicable product.

5. A DNA construct comprising:
   a) a gene which contains at least one intron;
   b) a cis-acting nucleotide sequence which is capable of rendering the removal of introns from a precursor transcript encoded by said gene, which gene includes at least one such cis-acting nucleotide sequence, occurring during the production of mRNA of said gene, dependent upon activation of a trans-acting factor, wherein said trans-acting factor being the RNA-activated protein kinase (PKR) which is capable of phosphorylating the α-subunit of eukaryotic initiation factor 2, operably linked to said gene; and c) optionally further comprising additional control, promoting and regulatory elements, and wherein said cis-acting nucleotide sequence is derived from the 3' untranslated region of the human tumor necrosis factor α gene (TNF-α-3'UTR) and consists of a sequence selected from the group consisting of SEQ ID NO:1 and SEQ ID NO:2.

6. The DNA construct according to claim 5 wherein said cis-acting nucleotide sequence is derived from the 3' untranslated region of the human tumor necrosis factor α gene (TNF-α-3'UTR) and consists of the nucleotide sequence as denoted by SEQ ID NO:1.

7. The DNA construct according to claim 5 wherein said cis-acting nucleotide sequence is derived from the 3' untranslated region of the human tumor necrosis factor α gene (TNF-α-3'UTR) and consists of the nucleotide sequence as denoted by SEQ ID NO:2.

8. A DNA construct according to any one of claims 5, 6 or 7 wherein said control, promoting and regulatory elements are suitable transcription promoters, transcription enhancers and mRNA destabilizing elements.

9. The DNA construct according to claim 5, wherein said gene which contains at least one intron, encodes a protein selected from the group consisting of enzymes, hormones, growth factors, cytokines, structural proteins, industrially applicable proteins, agriculturally applicable proteins, a protein which is a therapeutic product, protein which is an agricultural product, and a protein which is an industrially applicable product.

10. The DNA construct according to claim 9 wherein said nucleotide sequence is contained within an exon of said gene.

11. The DNA construct according to claim 9 wherein said nucleotide sequence is inserted within an intron of said gene.

12. The DNA construct according to claim 10 wherein said gene is the human TNF-α gene.

13. The DNA construct according to claim 12 being the plasmid pTNF-α, in which said cis-acting nucleotide sequence is contained within an exon of the human TNF-α gene.

14. The DNA construct according to claim 13 being the plasmid pTNF-α(3'UTR-αEP).

15. The DNA construct according to claim 5 wherein said gene is the human TNF-β gene.

16. The DNA construct according to claim 15 in which said cis-acting nucleotide sequence is contained within an exon of the human TNF-β gene.

17. The DNA construct according to claim 16 being the plasmid pTNF-β(3'UTR-α).

18. The DNA construct according to claim 16 being the plasmid pTNF-β(3'UTR-αEP).

19. The DNA construct according to claim 11 wherein the DNA construct is pTNFα(Δ3'UTR)i3EP.

20. A vector comprising the cis-acting nucleotide sequence according to claim 1 or the DNA construct according to claim 5 and a suitable DNA carrier, capable of transfecting a host cell with said cis-acting nucleotide sequence.

21. The vector according to claim 20 optionally further comprising additional expression, control, promoting and regulatory elements operably linked thereto.

22. The vector according to claim 21 wherein said carrier is salmon sperm DNA.

23. The vector according to claim 21 wherein said carrier is viral DNA.

24. A host cell transfected with the DNA construct according to claim 19.

25. A host cell transfected with the vector according to claim 20.

26. A host cell according to claim 24 being a eukaryotic or yeast cell.

27. The host cell according to claim 26 being a mammalian hemopoietic cell, fibroblast, epithelial cell, or lymphocyte.

28. The host cell according to claim 24 wherein said eukaryotic cell is the baby hamster kidney (BHK-21) cell line or the Chinese hamster ovary (CHO) cell line.

29. A composition comprising the expression vector according to claim 20.

30. A method for producing a transfected cell capable of producing a protein comprising a) transfecting a host cell with a DNA construct to give a host cell capable of expressing said protein, wherein said DNA construct comprises a) a gene which contains at least one intron, wherein said gene encodes said protein; b) a cis-acting nucleotide sequence which is capable of rendering the removal of introns from a precursor transcript encoded by said gene, which gene includes at least one such cis-acting nucleotide sequence, occurring during the production of mRNA of said gene, dependent upon activation of a trans-acting factor, wherein said trans-acting factor being the RNA-activated protein kinase (PKR) which is capable of phosphorylating the α-subunit of eukaryotic initiation factor 2, operably linked to said gene; and c) optionally further comprising additional control, promoting and regulatory elements, and wherein said cis-acting nucleotide sequence is derived from the 3' untranslated region of the human tumor necrosis factor αgene (TNF-α-3'UTR) and consists of a sequence selected from the group consisting of SEQ ID NO:1 and SEQ ID NO:2; and b) culturing the cell obtained in (a) under culture conditions amenable to express said protein.

31. A method of producing a protein comprising:

a) providing host cells transfected with a DNA construct, which are capable of expressing said protwherein said DNA construct comprises a) a gene which contains at least one intron, wherein said gene encodes said protein; b) a cis-acting nucleotide sequence which is capable of rendering the removal of introns from a precursor transcript encoded by said gene, which gene includes at least one such cis-acting nucleotide sequence, occurring during the production of mRNA of said gene, dependent upon activation of a trans-acting factor, wherein said trans-acting factor being the RNA-activated protein kinase (PKR) which is capable of phosphorylating the α-subunit of eukaryotic initiation factor 2, operably linked to said gene; and c) optionally further comprising additional control, promoting and regulatory elements, and wherein said cis-acting nucleotide sequence is derived from the 3' untranslated region of the human tumor necrosis factor α gene (TNF-α-3'UTR) and consists of a sequence selected from the group consisting of SEQ ID NO:1 and SEQ ID NO:2;

b) culturing the cells provided in (a) under culture conditions amenable to express said protein; and c) isolating said protein from the cell culture obtained in (b).

32. A composition comprising the host cell according to claim 27.

33. A method of producing a protein comprising:
a) transfecting a host cell with an expression vector to produce a host cell capable of expressing said protein, wherein said expression vector is selected from the group consisting of (1) a cis-acting nucleotide sequence which is capable of rendering the removal of introns from a precursor transcript encoded by any gene, which gene harbors at least one such cis-acting nucleotide sequence, occurring during the production of mRNA of said gene, dependent upon activation of a trans-acting factor, said trans-acting factor being the RNA-activated protein kinase (PKR) which is capable of phosphorylating the α-subunit of eukaryotic initiation factor 2, and wherein said cis-acting nucleotide sequence is derived from the 3' untranslated region of the human tumor necrosis factor α gene (TNF-α-3'UTR) and consists of a sequence of SEQ ID NO:1 or SEQ ID NO:2; and (2) a DNA construct comprising (A) a gene which contains at least one intron, wherein said gene encodes said protein; (B) a cis-acting nucleotide sequence which is capable of rendering the removal of introns from a precursor transcript encoded by said gene, which gene includes at least one such cis-acting nucleotide sequence, occurring during the production of mRNA of said gene, dependent upon activation of a trans-acting factor, wherein said trans-acting factor being the RNA-activated protein kinase (PKR) which is capable of phosphorylating the α-subunit of eukaryotic initiation factor 2, operably linked to said gene; and (C) optionally further comprising additional control, promoting and regulatory elements, and wherein said cis-acting nucleotide sequence is derived from the 3' untranslated region of the human tumor necrosis factor α gene (TNF-α-3'UTR) and consists of the sequence of SEQ ID NO: 1 or SEQ ID NO: 2 and a suitable DNA carrier;
b) culturing the cell obtained in (a) under culture conditions amenable to express said protein; and
c) isolating said protein from the cell culture obtained in (b).

34. A method of producing a protein comprising:
a) providing host cells transfected with an expression vector to produce a host cell capable of expressing said protein, wherein said expression vector is selected from the group consisting of (1) a cis-acting nucleotide sequence which is capable of rendering the removal of introns from a precursor transcript encoded by any gene, which gene harbors at least one such cis-acting nucleotide sequence, occurring during the production of mRNA of said gene, dependent upon activation of a trans-acting factor, said trans-acting factor being the RNA-activated protein kinase (PKR) which is capable of phosphorylating the α-subunit of eukaryotic initiation factor 2, and wherein said cis-acting nucleotide sequence is derived from the 3' untranslated region of the human tumor necrosis factor α gene (TNF-α-3'UTR) and consists of a sequence of SEQ ID NO:1 or SEQ ID NO:2; and (2) a DNA construct comprising (A) a gene which contains at least one intron, wherein said gene encodes said protein; (B) a cis-acting nucleotide sequence which is capable of rendering the removal of introns from a precursor transcript encoded by said gene, which gene includes at least one such cis-acting nucleotide sequence, occurring during the production of mRNA of said gene, dependent upon activation of a trans-acting factor, wherein said trans-acting factor being the RNA-activated protein kinase (PKR) which is capable of phosphorylating the α-subunit of eukaryotic initiation factor 2, operably linked to said gene; and (C) optionally further comprising additional control, promoting and regulatory elements, and wherein said cis-acting nucleotide sequence is derived from the 3' untranslated region of the human tumor necrosis factor α gene (TNF-α-3'UTR) and consists of the sequence of SEQ ID NO: 1 or SEQ ID NO: 2 and a suitable DNA carrier,
b) culturing the cells provided in (a) under culture conditions amenable to express said protein; and
c) isolating said protein from the cell culture obtained in (b).

35. A host cell according to claim 25 being a eukaryotic or yeast cell.

36. The host cell according to claim 35 being a mammalian hemopoietic cell, fibroblast, epithelial cell, or lymphocyte.

37. A composition comprising the host cell according to claim 36.

* * * * *